(12) United States Patent
Silverman et al.

(10) Patent No.: US 9,856,231 B2
(45) Date of Patent: Jan. 2, 2018

(54) TETRAHYDROTHIOPHENE-BASED GABA AMINOTRANSFERASE INACTIVATORS

(71) Applicant: Northwestern University, Evanston, IL (US)

(72) Inventors: Richard B. Silverman, Winnetka, IL (US); Hoang V. Le, Evanston, IL (US); Dustin D. Hawker, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/065,487

(22) Filed: Mar. 9, 2016

(65) Prior Publication Data

US 2016/0264544 A1    Sep. 15, 2016

Related U.S. Application Data

(60) Provisional application No. 62/130,219, filed on Mar. 9, 2015.

(51) Int. Cl.

| C07D 333/32 | (2006.01) |
|---|---|
| C07D 333/48 | (2006.01) |
| C07D 333/40 | (2006.01) |
| C12N 9/99 | (2006.01) |

(52) U.S. Cl.
CPC ............ *C07D 333/40* (2013.01); *C12N 9/99* (2013.01)

(58) Field of Classification Search
CPC ... C07D 333/36; C07D 333/32; C07D 333/48
USPC ........................................................ 549/68
See application file for complete search history.

(56) References Cited

U.S. PATENT DOCUMENTS 4,520,028 A    5/1985    Adams et al.
6,794,413 B1 *  9/2004   Silverman ............ A61K 31/557
                                                            514/573

OTHER PUBLICATIONS

Allan, Aust. J. Chem., 1984, vol. 37, pp. 1123-1126.*
Kitz, R. et al., "Esters of Methanesulfonic Acid as Irreversible Inhibitors of Acetylcholinesterase", J. Biol. Chem., 1962, 237, 3245-3249.
Walker, D. et al., "Synthesis of (±)-8-Oxa-3-azabicyclo[3.2.1]octan-2-thione and (±)-2-Oxa-5-azabicyclo[2.2.1] heptan-6-thione: Potential Synthons for the Preparation of Novel Heteroaryl-Annulated Bicyclic Morpholines", Synthesis (Stuttg)., 2011 (07), 1113-1119.
Evans, C. et al., "Synthesis of Either Enantiomer of cis-3-Aminocyclopentanecarboxylic Acid from Both Enantiomers of Racemic 2-Azabicyclo[2.2.1] hept-5-en-3-one", A. G. J. Chem. Soc., Perkin Trans. 1, 1991, 656-657.
Forró, E. et al., "Enzymatic Method for the Synthesis of Blockbuster Drug Intermediates—Synthesis of Five-Membered Cyclic γ-Amino Acid and γ-Lactam Enantiomers", Eur. J. Org. Chem., 2008, 5263-5268.
Koo, Y. K. et al., "The Multiple Active Enzyme Species of g-Aminobutyric Acid Aminotransferase Are Not Isozymes", Arch Biochem. Biophys., 2000, 374, 248-254.
Yung Chi, C. et al., "Relationship Between the Inhibition Constant (KI) and the Concentration of Inhibitor which Causes 50 per cent Inhibition (I50) of an Enzymatic Reaction", Biochem. Pharmacol., 1973, 22, 3099-3108.
Chebib, M. et al., "The effects of cyclopentane and cyclopentene analogues of GABA at recombinant GABAc receptors", European Journal of Pharmacology, 2001, vol. 430, pp. 185-192.
Allan, R. et al., "Synthesis of Analogues of GABA. Xii* cis- and trans-4-Aminotetrahydrofuran-2-carboxylic Acid", Aust. J. Chem., 1984, vol. 37, pp. 1123-1126.
Armishaw, C. et al., "Rational Design of α-Conotoxin Analogues Targeting α7 Nicotinic Acetylcholine Receptors", The Journal of Biological Chemistry, Apr. 3, 2009, vol. 284, No. 14, pp. 9498-9512.
Le, H.V. et al., "Design and Mechanism of Tetrahydrothiophene-based GABA Aminotransferase Inactivators", J Am Chem Soc., Apr. 8, 2015, vol. 197, No. 13, pp. 4525-4533.
International Search Report and Written Opinion for PCT/US2016/021565 dated Aug. 29, 2016, 16 pages.

* cited by examiner

*Primary Examiner* — Yong Chu
*Assistant Examiner* — Sonya Wright
(74) *Attorney, Agent, or Firm* — Andrus Intellectual Property Law, LLP

(57) ABSTRACT

Tetrahydrothiophene and related heterocyclic analogs and related methods for GABA aminotransferase inactivation.

11 Claims, 11 Drawing Sheets

TETRAHYDROTHIOPHENE-BASED GABA AMINOTRANSFERASE INACTIVATORS

This application claims priority to and the benefit of application Ser. No. 62/130,219 filed Mar. 9, 2015, the entirety of which is incorporated herein by reference.

This invention was made with government support under grant number RO1 DA030604 awarded by the National Institutes of Health. The government has certain rights in the invention.

BACKGROUND OF THE INVENTION

Epilepsy is a family of chronic neurological disorders characterized by recurring convulsive seizures, which result from abnormal, excessive neuronal activity in the central nervous system. It is estimated that about 65 million people worldwide have epilepsy. Epilepsy can arise from an imbalance in two major neurotransmitters that regulate brain neuronal activity, L-glutamate, an excitatory neurotransmitter, and γ-aminobutyric acid (GABA), an inhibitory neurotransmitter.

GABA is produced in GABAergic neurons from L-glutamate by the enzyme glutamic acid decarboxylase (GAD) (FIG. 1). GABA is then released into the synapse and transported to glial cells. The enzyme GABA aminotransferase (GABA-AT) in glial cells degrades GABA to succinic semialdehyde (SSA), which is further oxidized to succinate and enters the Krebs cycle. GABA-AT also converts α-ketoglutarate from the Krebs cycle to L-glutamate. Because there is no GAD in glial cells, this newly formed L-glutamate is not converted to GABA. It is instead converted to L-glutamine, which is then released from glial cells into the synapse and transported back to GABAergic neurons to complete the metabolic cycle of L-glutamate.

Low levels of GABA are linked to not only epilepsy, but also many other neurological disorders including Parkinson's disease, Alzheimer's disease, Huntington's chorea, and cocaine addiction. Raising GABA levels has proven effective in stopping recurring convulsive seizures in the treatment of epilepsy. However, GABA does not cross the blood-brain barrier (BBB); therefore, an increase in brain levels of GABA cannot be achieved by intravenous administration. Other possible routes to increased brain levels of GABA include enhancing the activity of GAD, the enzyme that makes GABA, inhibiting the activity of GABA-AT, the enzyme that degrades GABA, and inhibiting the reuptake of GABA by blocking the action of the GABA transporters.

One approach relates to the design of mechanism-based inactivators of GABA-AT; in particular, the design of unreactive compounds that require GABA-AT catalysis to convert them into a species that inactivates the enzyme. Because these molecules are not initially reactive, but require the catalytic activity of GABA-AT to become activated and form covalent bonds, indiscriminate reactions with off-target proteins, leading to undesired side effects, should be greatly reduced. Even at lower dosages, these inactivators can achieve the desired pharmacologic effects with enhanced potency and selectivity than conventional inhibitors.

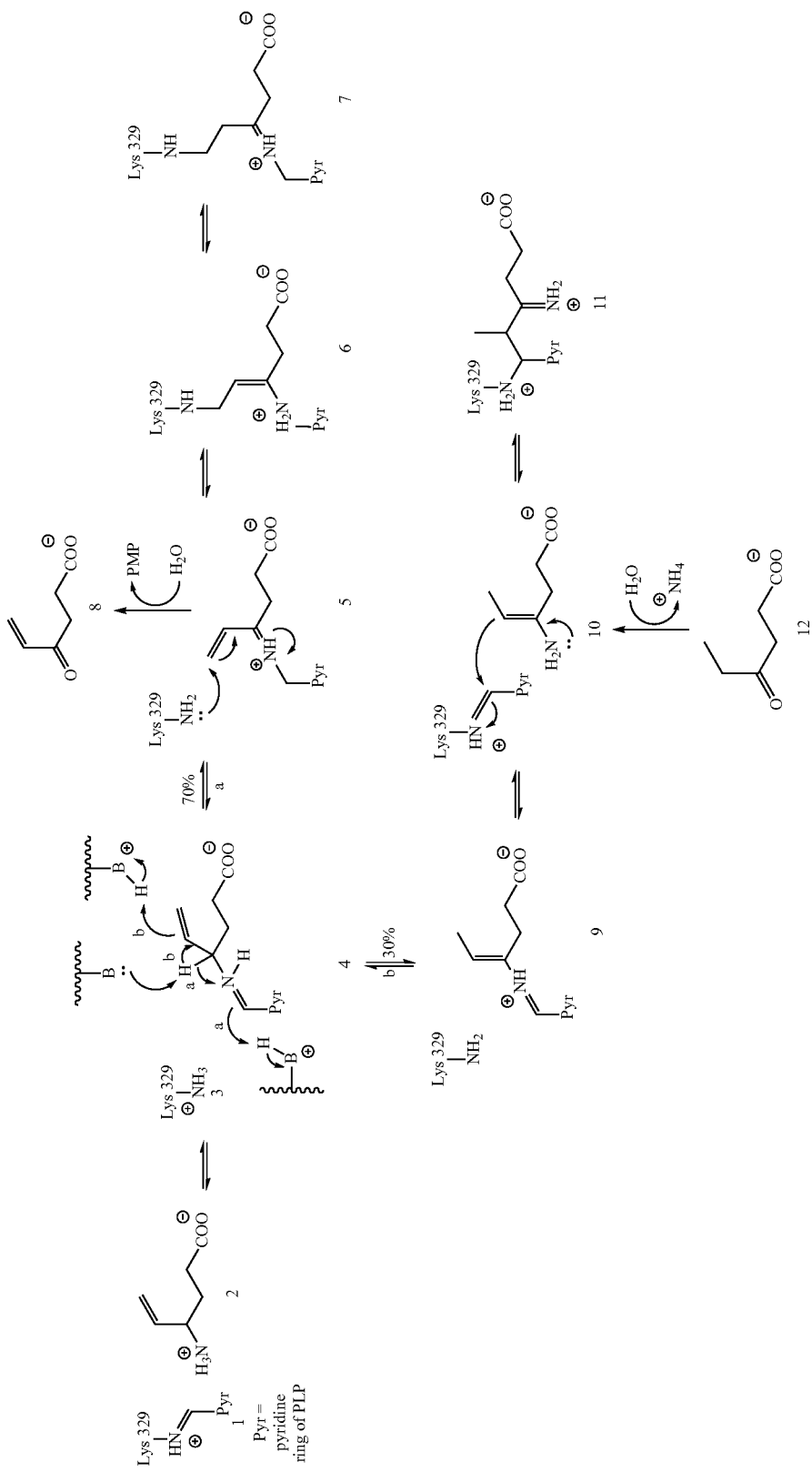

Currently, the only FDA-approved inactivator of GABA-AT is the drug vigabatrin (2) (Scheme 1), which was first developed by Lippert et al., and is used for the treatment of epilepsy. However, a large dose of vigabatrin (~1-3 g) needs to be taken daily, and there are many serious side effects that arise from its usage, including psychosis and permanent vision loss resulting from the damage of the retinal nerve fiber layer. As a result, the search for an alternative to vigabatrin in the treatment of epilepsy has been an ongoing concern in the art.

It has been determined that vigabatrin inactivates GABA-AT via two pathways: a Michael addition mechanism and an enamine mechanism, as shown in Scheme 1. In the Michael addition mechanism, the resulting Schiff base (4) from the reaction of vigabatrin and the lysine-bound PLP (1) on GABA-AT is subjected to γ-proton removal and tautomerization that leads to ketimine 5. An active-site nucleophile then reacts with Michael acceptor 5 to form 6, which is in equilibrium with 7. In the enamine mechanism, the Schiff base (4) is subjected to γ-proton removal and tautomerization through the vinyl bond, which leads to the release of enamine 10. Subsequent nucleophilic addition of 10 to the lysine-bound PLP on GABA-AT gives rise to 11.

The Michael addition mechanism and the enamine mechanism happen concurrently in a 70/30 ratio, respectively. It was discovered that ketimine 5 in the Michael addition mechanism, and enamine 10 in the enamine mechanism, underwent partial hydrolysis to form the α,β-unsaturated ketone (8) and the saturated ketone (12), respectively. While 8 is a reactive electrophile, possibly responsible for some side effects, 12 is not a reactive metabolite. From these findings, further study has been directed to vigabatrin analogs that either follow the enamine mechanism exclusively to avoid the formation of 8 or speed up the Michael addition pathway so that 5 would have much lower probability to undergo hydrolysis.

An energy minimized molecular model of vigabatrin bound to PLP in GABA-AT revealed that after tautomerization, the vinyl bond in 5 needs to rotate toward Lys-329 for the Michael addition to occur. Therefore, conformationally-restricted analogs such as 13 and 14 (FIG. 2) would prevent the rotation of the vinyl bond, thereby blocking the Michael addition mechanism. Experiments showed that 13 inactivated GABA-AT following the enamine mechanism exclusively. However, its potency remained low. In the alternative approach, conformationally-restricted analogs 15 and 16 have the vinyl bond readily pointed toward Lys-329 for rapid Michael addition to occur, thereby minimizing the hydrolysis of the ketimine intermediate. Experiments showed that 16 was 186 times more efficient in inactivating GABA-AT than vigabatrin. Furthermore, unlike vigabatrin, 16 did not inactivate or inhibit off-target enzymes, such as alanine aminotransferase and aspartate aminotransferase, and therefore is less likely to produce side effects. Indeed, 16 was tested in a multiple-hit rat model of infantile spasms, and the results showed that 16 suppressed spasms at doses of 0.1-1 mg/kg/day, which were >100-fold lower than those for vigabatrin. The spasms suppression by 16 stayed effective longer (3 days vs. 1 day for vigabatrin), and 16 also had a much larger margin of safety than vigabatrin.

SUMMARY OF THE INVENTION

In light of the foregoing, it is an object of the present invention to provide compounds, compositions and related methods of use for the selective inactivation of GABA-AT, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule compounds exhibiting GABA aminotranferase inactivation.

It can be another object of the present invention to provide one or more such compounds for in vitro use and study under conditions indicative of one or more mammalian disease states.

Alternatively, it can also be an object of the present invention to provide one or more such compounds enabling in vivo treatment of such disease states.

It can also be an object of the present invention to provide one or more such compounds with structural features facilitating interaction with and inactivation of GABA-AT.

It can also be an object of the present invention, alone or in conjunction with one or more of the foregoing objects, to provide a compound or composition for GABA-AT inhibition or inactivation, modulation of GABA-AT activity and/or treatment of epilepsy and various other neurological disorders and indications.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can be directed to a compound of a formula

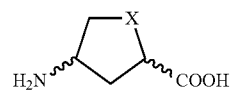

wherein X can be selected from S, $SO_2$, $CH_2$, O, and NR, where R can be selected from H and $C_1$- about $C_6$ alkyl moieties, including without limitation such straight-chain and branched alkyl moieties, or a salt thereof. In certain embodiments, X can be S. Without limitation in certain such embodiments, the amino and carboxy substituents can have a cis or trans stereochemical relationship.

In part, the present invention can also be directed to a compound of a formula

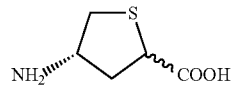

wherein in the amino and carboxy substituents can have either a cis or trans relationship, or a salt thereof. In certain embodiments, such a compound can be of a formula

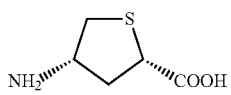

wherein the amino and carboxy substituents can have a cis stereochemical relationship, or a salt thereof.

Regardless, compounds useful in conjunction with this invention are without stereochemical or configurational limitation. As illustrated and discussed below, such compounds and/or their intermediates are available as single enantiomers, racemic mixtures from which isomers can be resolved, or diastereomers from which the corresponding enantiomers can be separated. Accordingly, any stereocenter can be (S) or (R) with respect to any other stereocenter(s). The amino and carboxy substituents can have either a cis or trans stereochemical relationship. As another separate consideration, various compounds can be present as an acid salt, either partially or fully protonated. In certain such embodiments, with respect to an ammonio substituent, the counter ion can be a conjugate base of a protic acid. In certain such or other embodiments, with respect to a carboxylate substituent, the counter ion can be an alkaline, alkaline-earth or ammonium cation. As described below, such a compound can be an amino acid hydrochloride. Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can be directed to a method for the treatment of a neurological disorder in a subject in need thereof. Such a method can comprise administering to such a subject a compound of a formula

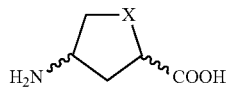

wherein X can be selected from S, $SO_2$, $CH_2$, O, and NR, where R can be selected from H and $C_1$- about $C_6$ alkyl moieties, including without limitation such straight-chain and branched alkyl moieties, or a salt thereof. In certain embodiments, X can be S. Without limitation, in certain such embodiments, the amino and carboxy substituents can have a cis or trans stereochemical relationship.

In part, the present invention can be directed to a method for the treatment of a neurological disorder in a subject in need thereof. Such a method can comprise administering to such a subject a compound of a formula

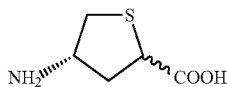

wherein the amino and carboxy substituents can have either a cis or a trans stereochemical relationship, or a salt thereof. Without limitation, in certain such embodiments, the amino and carboxy substituents can have a cis stereochemical relationship.

In part, the present invention can also be directed to a method of reducing or modulating activity of a GABA aminotransferase. Such a method can comprise providing a compound of the sort discussed above or described elsewhere herein; and contacting such a compound with a medium comprising GABA aminotransferase with an amount of such a compound effective to reduce or modulate GABA aminotransferase activity. Such a method can thereby reduce or modulate succinic semialdehyde and/or glutamate production in such a medium. In certain embodiments, such a compound can be provided as part of a pharmaceutical composition. Regardless, such contact can be in vitro or in vivo.

More generally, the present invention can also be directed to a method of reducing or modulating activity of GABA aminotransferase expressed by a glial cell. Such a method can comprise providing a compound of the sort discussed above or described elsewhere herein; and contacting such a compound with a cellular medium comprising glial cells with an amount of such a compound effective to reduce or modulate GABA aminotransferase activity. Such a method can thereby reduce or modulate succinic semialdehyde and/or glutamate production in such a cellular medium. In certain embodiments, such a compound can be provided as part of a pharmaceutical composition. Regardless, such contact can be in vitro or in vivo.

More generally, the present invention can also be directed to a method inhibiting or inactivating a GABA aminotransferase. Such a method can comprise providing a compound of the sort discussed above or described below, whether or not part of a pharmaceutical composition, and administering an effective amount of such a compound for contact with a GABA aminotransferase. Such contact can be, as would be understood in the art, for experimental and/or research purposes or as may be designed to simulate one or more in vivo or physiological conditions. Such compounds can include but are not limited to those illustrated by the following examples, referenced figures, incorporated references and/or accompanying synthetic schemes. In certain such embodiments, such a compound and/or combination thereof can be present in an amount at least partially sufficient to inactivate GABA-AT, or inhibit or modulate GABA degradation.

Figure 1:
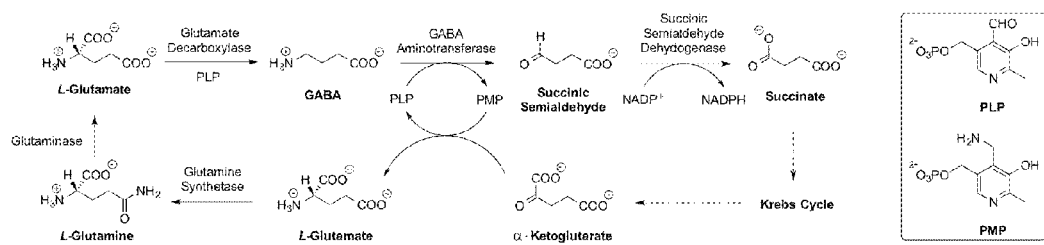
FIG. 1. Metabolic cycle of L-glutamate.
Figure 2:
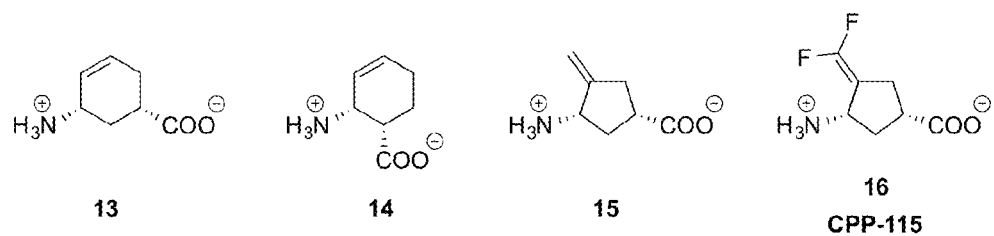
FIG. 2. Vigabatrin analogs (prior art) that follow one GABA-AT inactivation mechanism exclusively.
Figure 3:
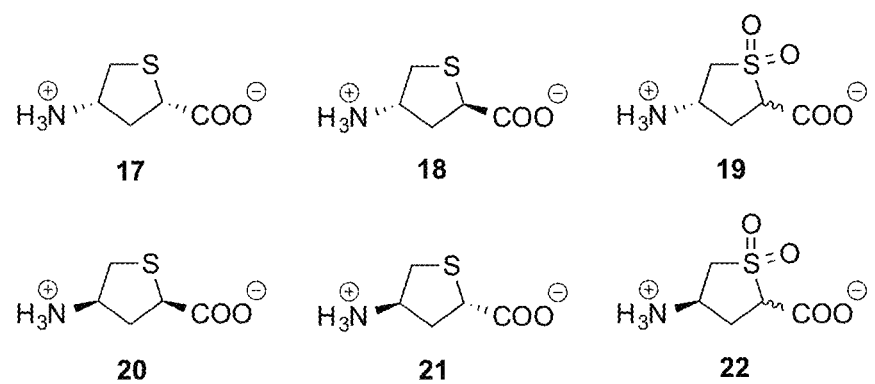
FIG. 3. Tetrahydrothiophene-based GABA analogs, in accordance with certain embodiments of this invention.

ine mechanism. To demonstrate certain non-limiting embodiments of this invention, a series of conformationally-restricted, tetrahydrothiophene-based analogs (FIG. 3) was synthesized. Such compounds have a properly-positioned leaving group that could facilitate a ring-opening mechanism in the inactivation of GABA-AT (Scheme 2). As described below, the synthesis, biological evaluation, mechanistic studies, including mass spectral and X-ray crystallographic results of these analogs reveal an unexpected inactivation mechanism.

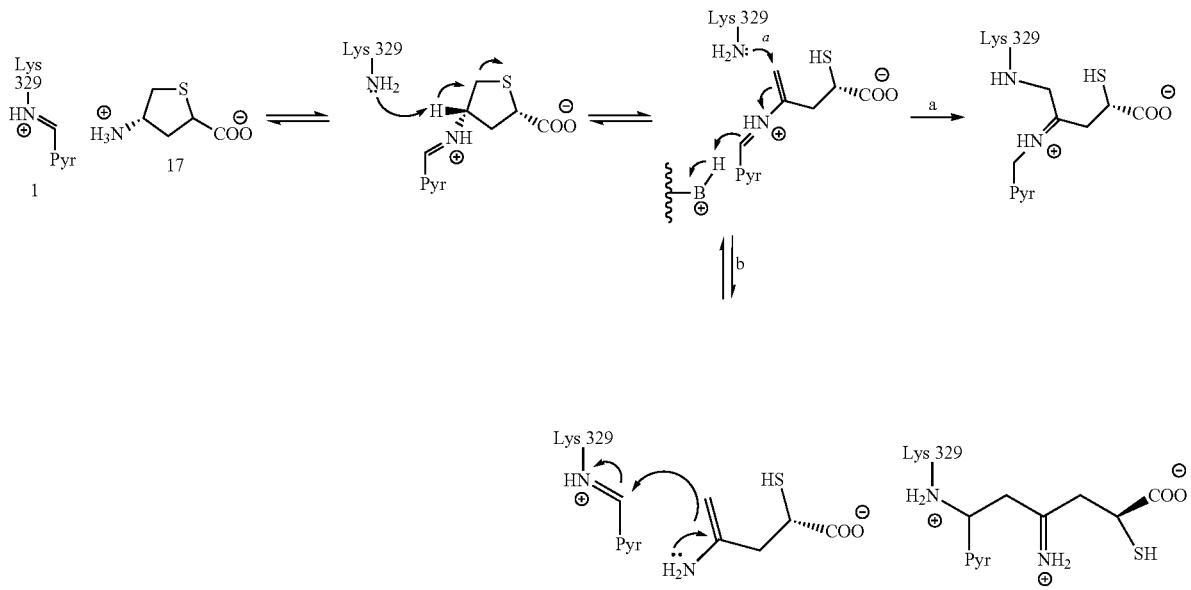

Pyr = pyridine ring of PLP

Fractions were collected each minute and counted for radioactivity. A solution of 1 mM PMP and 1 mM PLP was treated identically as a control.

Figure 7:
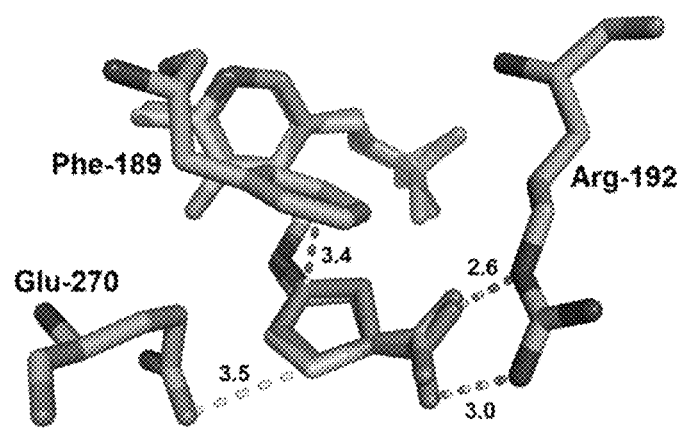

FIG. 7. Overlay of in silico model of compound PLP-39 adduct and PLP-17 adduct, as well as key nearby residues.

Figure 8A:
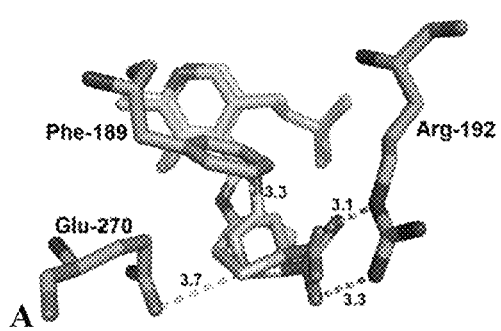
Figure 8B:
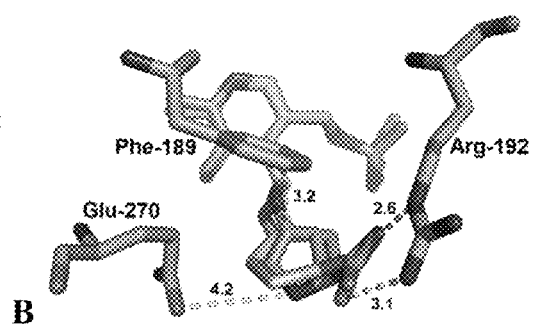

FIGS. 8A-B. (A) Overlay of in silico model of compound PLP-40 adduct and PLP-17 adduct, (B) Overlay of in silico model of compound PLP-41 adduct and PLP-17 adduct.

Figure 9:
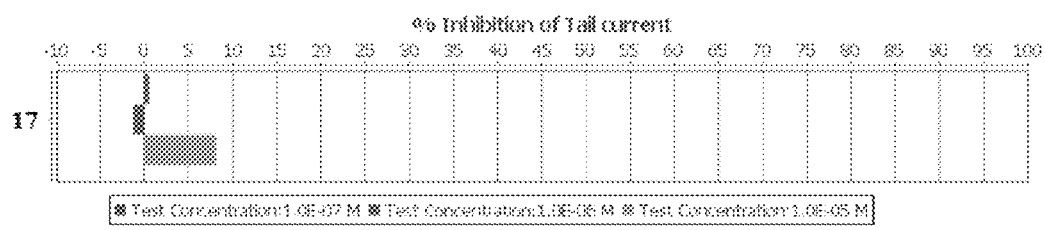

FIG. 9. Inhibition of the hERG channel by 17 (hERG CHO-K1 cell line, detection method: automated patch-clamp).

Figure 10:
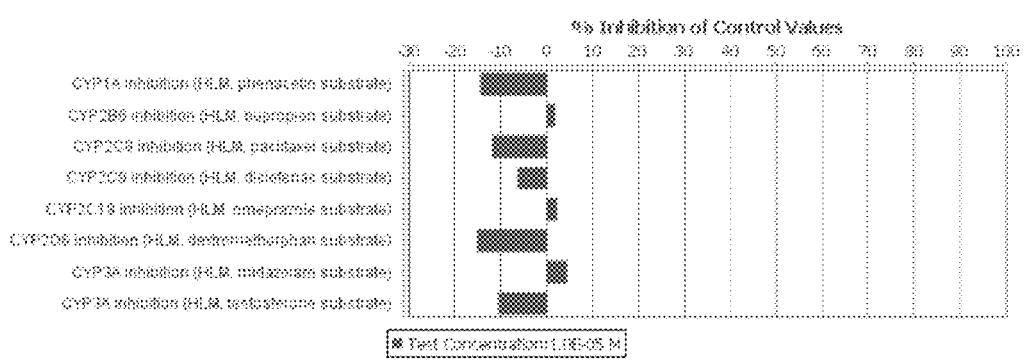

FIG. 10. Inhibition of microsomal cytochromes P450 by 17.

Figure 11A:
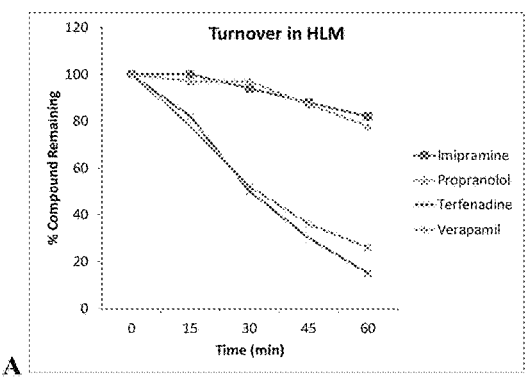
Figure 11B:
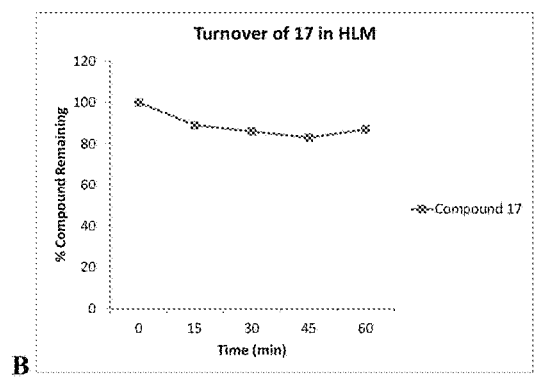

FIGS. 11A-B. Time-dependent Loss of (A) imipramine, propranolol, terfenadine, and verapamil and (B) 17 in human liver microsomes (HLM).

DETAILED DESCRIPTION OF CERTAIN EMBODIMENTS

As part of an ongoing effort to develop antiepileptic drugs, there is continued interest in new GABA analogs that inactivate GABA-AT by new mechanisms. Compounds with a leaving group adjacent to the carbanion formed after the γ-proton removal seem to inactivate GABA-AT by an enam- The syntheses of analogs 17-19 are shown in Scheme 3, starting from commercially available D-cysteine methyl ester hydrochloride (23). The route up to the generation of dihydrothiophene 28 was achieved by following a modified procedure from Adam et al. Reduction of 28 by magnesium in methanol resulted in diastereomers 29 and 30, which were separable by flash column chromatography. Deprotection of the amino group and hydrolysis of the ester in 29 and 30 using aqueous HCl provided the desired analogs 17 and 18, respectively. Oxidation of 29 or 30 by MnSO$_4$ and H$_2$O$_2$ resulted in a 1:1 mixture of the corresponding sulfones (31) as a result of epimerization at the C-2 position. Subsequent deprotection of the amino group and hydrolysis of the ester in 31 using aqueous HCl gave desired analog 19. Synthesis of compounds 20-22 followed an identical route starting from L-cysteine methyl ester hydrochloride. The purity of compounds 17-22 was confirmed by HPLC and HRMS, which showed that there was none of the corresponding dihydrothiophene analog of 17, a known inactivator of GABA-AT.

Scheme 3. Syntheses of GABA Analogs 17-19

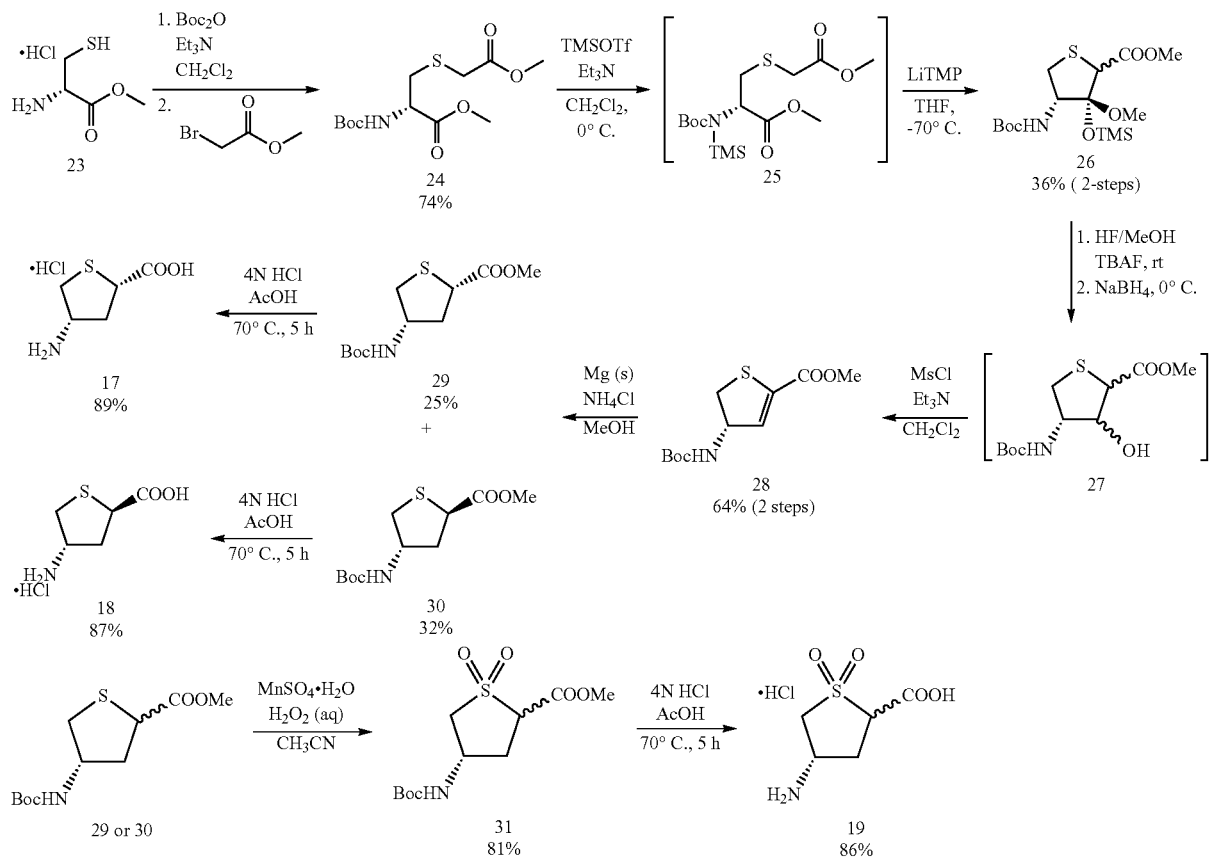

Preliminary in vitro results showed that 19-22 were weak reversible inhibitors, while 17 and 18 were potent inactivators of GABA-AT (Table 1). The kinetic constants for inactivation of GABA-AT by 17 and 18 could not be determined accurately under optimal conditions (pH 8.5, 25° C.), where the enzyme exhibited maximum activity, because inactivation occurred too rapidly. The kinetic constants for inactivation of GABA-AT by 17 and 18 were instead measured under non-optimal conditions (pH 6.5, 25° C.) using a Kitz and Wilson replot. (Kitz, R.; Wilson, I. B. *J. Biol. Chem.* 1962, 237, 3245-3249.) From $k_{inact}/K_I$ values (Table 1), it was concluded that 17 is eight times more efficient an inactivator of GABA-AT than vigabatrin (with an inactivation rate constant almost 20 times that of vigabatrin), and 18 is half as efficient as vigabatrin.

TABLE 1

Kinetic constants for the inhibition and inactivation of GABA-AT by 17-19

| Compound | $K_I$ (mM) | $K_{inact}$ (min$^{-1}$) | $K_{inact}/K_I$ (min$^{-1}$ mM$^{-1}$) | $K_i$ (mM) |
|---|---|---|---|---|
| 17 | 0.182 | 0.17 | 0.93 | — |
| 18 | 2.23 | 0.12 | 0.05 | — |
| 19 | — | — | — | 3.2 ± 0.7 |
| 20 | — | — | — | 3.4 ± 0.8 |
| 21 | — | — | — | 3.3 ± 0.7 |
| 22 | — | — | — | 7.5 ± 0.7 |
| (S)-vigabatrin | 3.2 | 0.37 | 0.11 | — |

Figure 4A:
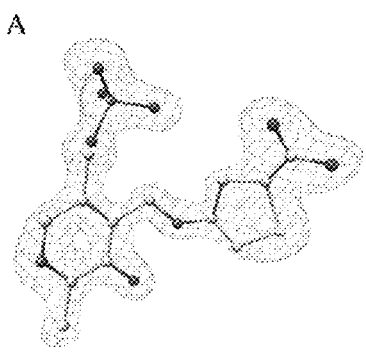
FIGS. 4A-C. The PLP-dihydrothiophene complex, shown in ball-and-stick form, is the final adduct, which contains a nonplanar dihydrothiophene ring. (A) The electron density of the simulated-annealing omit map ($F_O-F_C$) is shown as a gray mesh at 3.5σ around the PLP-dihydrothiophone adduct. (B, C) Two different orientations of the same image, displaying (B) the refined atom positions and (C) the buckled ring plane. The electron density of the simulated omit map $(F_O-F_C)$ is shown in a mesh at 4.16 around atoms in the dihydrothiophene ring (at a radius of 0.6 Å).
Figure 4B:
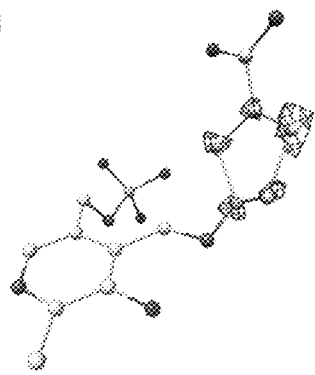
Figure 4C:
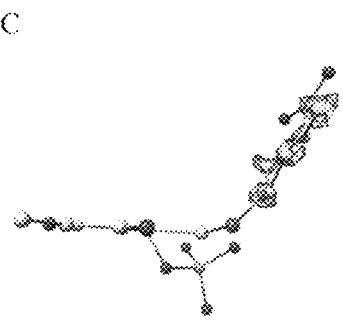
Figure 5A:
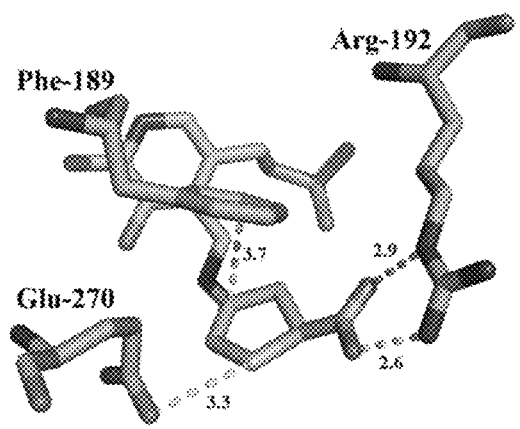
FIGS. 5A-B. (A) Interactions between the PLP-dihydrothiophene adduct and nearby residues. (B) Directionality of the intermolecular weak nonbonded S . . . O interaction in theoretical studies, representing an $\pi_O \rightarrow \sigma_s^*$ orbital interaction.
Figure 5B:
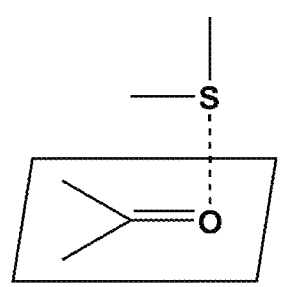

The X-ray crystal structure GABA-AT inactivated by 17 (at 1.66 Å) showed that the inactivating metabolite contained a buckled 5-membered ring covalently bound to PLP, and Lys-329 was not covalently modified. The final ligand interpretation is strongly supported by the electron density of the simulated annealing omit map ($F_O$-$F_C$, FIG. 4A). Furthermore, the omit map density at a higher contour level also revealed that the refined atom positions of the dihydrothiophene ring were accurate, resulting in a nonplanar ring (FIG. 4B,C). (S)-4-Amino-4,5-dihydro-2-thiophenecarboxylic acid, the corresponding dihydrothiophene analogue of 17, is a known inactivator of GABA-AT that inactivates by an aromatization mechanism resulting in a thiophene ring; it also is an inactivator of aspartate aminotransferase. Here, the crystal structure of 17-inactivated GABA-AT suggests that the inactivation of GABA-AT by 17 is likely to follow the mechanism shown in Scheme 4. The resulting Schiff base (32) from the reaction of 17 and the lysine-bound PLP on GABA-AT undergoes γ-proton removal, leading to enamine 34. The crystal structure revealed that 34 was stabilized in the active site by an interaction between its carboxylate group and the guanidinum group of Arg-192, by the interaction between the enamine alkene and the phenyl ring of Phe-189, and the sulfur atom in 34 is in close proximity (3.3 Å) to a carboxyl oxygen atom of Glu-270 (FIG. 5A). Without limitation to any one theory or mode of operation, this distance suggests a weak nonbonded interaction between the divalent sulfur and the carboxyl carbonyl oxygen. Weak nonbonded S . . . O and S . . . N interactions have been reported, but are mainly characterized as stabilizing forces of protein structures and of some organic sulfur compounds. Until now, all reported weak nonbonded interactions have been intramolecular. It is believed that no intermolecular weak nonbonded S . . . O and S . . . N interactions have been reported. However, the distance and directionality of intermolecular nonbonded S . . . O interactions has been suggested in theoretical studies. For intermolecular nonbonded S . . . O interactions, the nucleophilic O atom approaches the S atom from the backside of the S—Y and S—Z bonds (the $\sigma_s^*$ direction), and the S atom lies in the direction of the π orbital of O (the $\pi_O$ direction) (FIG. 5B). The stabilization of this S . . . O═C interaction is described by an $\pi_O \rightarrow \sigma_s^*$ orbital interaction, and 3.3 Å is well within the predicted distance. As shown in FIG. 5A, the directionality of the interaction between the sulfur atom in metabolite 34 and the carboxyl group of Glu-270 matches the description of the directionality of theoretical intermolecular nonbonded S . . . O interactions. Therefore, the interaction between the sulfur atom in metabolite 34 and the carboxyl group of Glu-270 might be the first reported example of an intermolecular nonbonded S . . . O interaction, which contributes to the stabilization of metabolite 34 in the active site of GABA-AT.

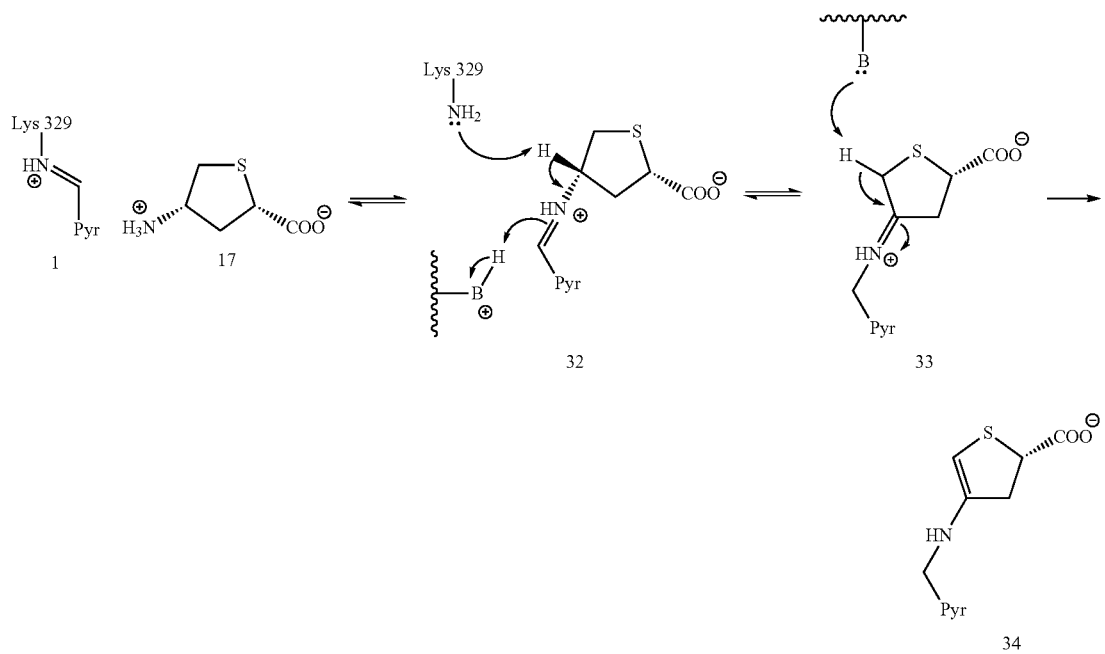

Scheme 4. Proposed mechanism for the inactivation of GABA-AT by 17

Pyr = pyridine ring of PLP

Metabolomics (via ESI-mass spectrometry) was run on a sample of GABA-AT, inactivated by 17, but the presence of 34 was not observed. (See Example 18.) When a small amount of formic acid was added to another sample of GABA-AT inactivated by 17 to disrupt H-bonding before running the spectrum, metabolite 36 was detected instead of 34. Through mass spectral analysis, fragmentation data for m/z 144.9954 confirmed the structure of 36, the likely result of hydrolysis of 34 (Scheme 5).

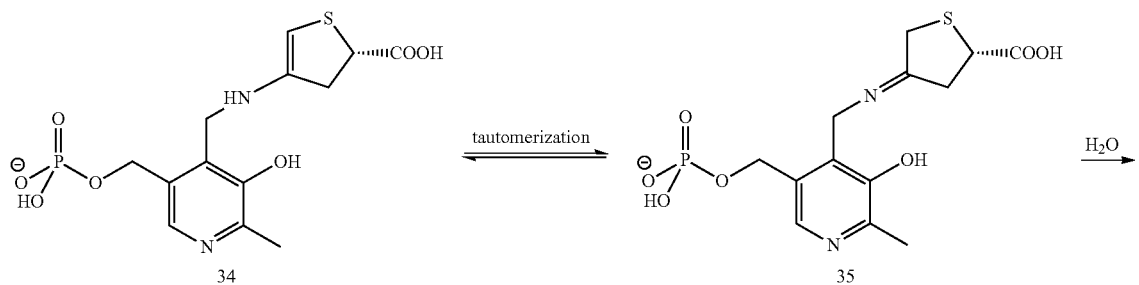

Scheme 5. Hydrolysis of Metabolite 34

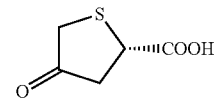

36

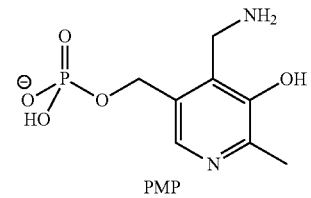

PMP

Figure 6:
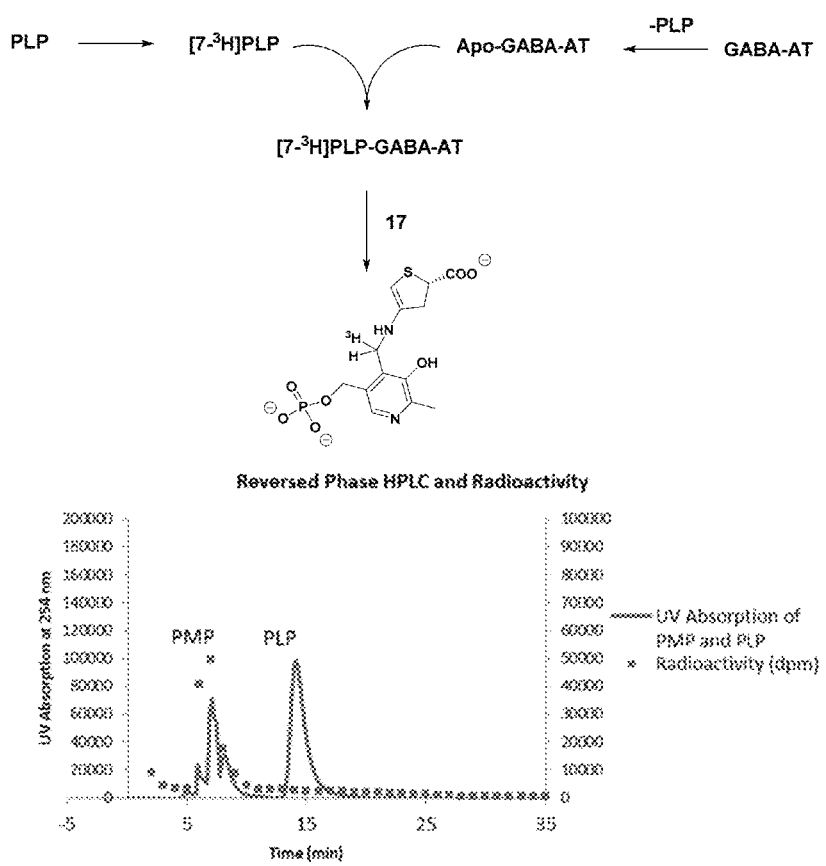
FIG. 6. Radioactive-labeling experiment for the inactivation of GABA-AT by 17: [7-$^3$H]PLP-GABA-AT was prepared from apoGABA-AT and [7-$^3$H]PLP then inactivated by 17, followed by denaturation and submission to HPLC.

Treatment of [7-³H]PLP-reconstituted GABA-AT with 17 was performed to determine the fate of the coenzyme upon inactivation. (See Examples 15-17.) A solution of 1 mM PMP and 1 mM PLP was treated identically as controls. The results showed that the denaturation of GABA-AT, inactivated by 17, released PMP exclusively (FIG. 6).

Results from the radioactive-labeling experiment and metabolomics suggested that metabolite 34 was not stable outside of the active site and would undergo hydrolysis to produce PMP and 36, supporting the proposed mechanism for the inactivation of GABA-AT by 17 shown in Scheme 4.

If the interaction between the sulfur atom in 34 and the O=C of Glu-270 is an intermolecular nonbonded S . . . O interaction, then the corresponding cyclopentane analog (39) (Scheme 6) should form a less stable metabolite in the active site of GABA-AT than 34. Compound 39 was synthesized from (1S,4R)-2-azabicyclo-[2.2.1]hept-5-en-3-one (37) (Scheme 6) and its activity was investigated. The results showed that 39 is not an inactivator but is a good competitive inhibitor of GABA-AT with a $K_i$ of 0.87 mM. A computer model of the energy-minimized hypothetical adduct of 39 bound to PLP after tautomerization and deprotonation (i.e., the cyclopentene analogue of 34) docked into GABA-AT using GOLD gave the pose with the highest fitness score that was almost identical to that shown in FIG. 5B (FIG. 7). These inhibition and modeling results further support the role of the sulfur atom in retaining the product in the active site of GABA-AT, thereby inactivating the enzyme.

Scheme 6. Synthesis of Cyclopentane Analog 39

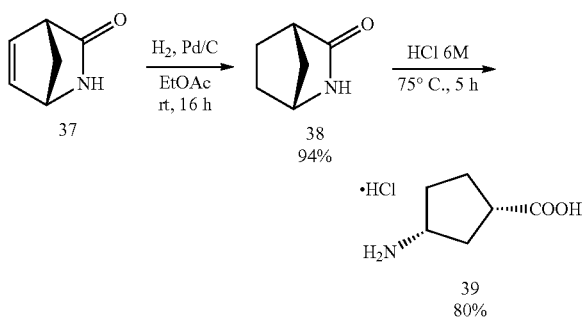

Two corresponding tetrahydrofuran and tetrahydropyrrole analogs, 40 and 41, respectively, were also synthesized, and their activities were investigated. Depending on the local pH in the active site of GABA-AT, there might be a H-bond between the O atom or NH of the analogs and the carboxyl group of Glu-270, which might result in a tighter binding of the final metabolite to the active site.

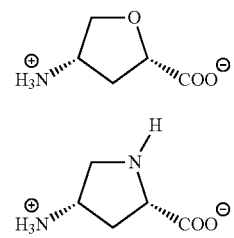

Computer modeling for the energy-minimized hypothetical PLP-40 adduct and PLP-41 adducts was carried out. These adducts were docked into GABA-AT (FIGS. 8A and 8B, respectively). The pose with the highest fitness score of the PLP-40 adduct places the oxygen atom in the PLP-40 adduct at a farther distance from the oxygen atom in Glu-270 than the corresponding distance between the sulfur atom in the crystal structure of the PLP-17 adduct and the oxygen atom in Glu-270. This may be that the negative charge on the carboxylate of Glu-270 repulses the partial negative charge on the oxygen atom in the PLP-40 adduct. The pose with the highest fitness score of the PLP-41 adduct places the nitrogen atom in the PLP-41 adduct at an even farther distance from the oxygen atom in Glu-270 than the corresponding distance between the sulfur atom in the crystal structure of the PLP-17 adduct and the oxygen atom in Glu-270. With a distance of 4.2 Å, it is unlikely that there is a hydrogen bond interaction between the nitrogen atom in the PLP-41 adduct and the oxygen atom in Glu-270. In both poses of the PLP-40 adduct and the PLP-41 adduct, the tetrahydrofuran ring and the tetrahydropyrrole ring are smaller than the tetrahydrothiophene ring, which forces the angles of the carboxylate groups on these rings closer to 109.5°. Since the PLP-40 adduct and the PLP-41 adduct likely favor the interaction with Arg-192, they would place the oxygen atom and nitrogen atom at farther distances from Glu-270, as the poses suggested.

Compound 40 was synthesized, starting from commercially available 4,5-dibromo-2-furoic acid (42) (Scheme 7). Selective debromination of 42 using zinc metal, followed by esterification, provided 43. Direct copper-catalyzed amidation of 43 with tert-butyl carbamate, under Buchwald conditions, generated 44. The reduction of 44 by Rh/C resulted in cis-products exclusively, just as reported by Walker et al. (Walker, D.; Wishka, D.; Beagley, P.; Turner, G.; Solesbury, N. *Synthesis (Stuttg).* 2011, 2011 (07), 1113-1119.) A mixture of enantiomers 45 and 46 was hydrolyzed and then coupled with (−)-menthol to provide a mixture of diastereomers 49 and 50. HPLC using a C18 column, a C8 column, or a semi-prep Whelk-O 1 chiral column failed to separate 49 and 50. Subsequent hydrolysis and deprotection of the Boc group in 49 and 50 gave a mixture of enantiomers 40 and 51. 1D NOE (not shown) confirmed that the carboxylic group and the amino group were on same side of the tetrahydrofuran ring. Meanwhile, the Boc groups in enantiomers 45 and 46 were deprotected, and the resulting amines 52 and 53 were coupled with (S)-(+)-Mosher acid chloride to afford diastereomeric amides 54 and 55, which were separated by HPLC using a semi-prep Whelk-01 chiral column. Subsequent 2-step hydrolysis of 54 and 55 with LiOH and HCl 6M afforded 40 and 51, respectively.

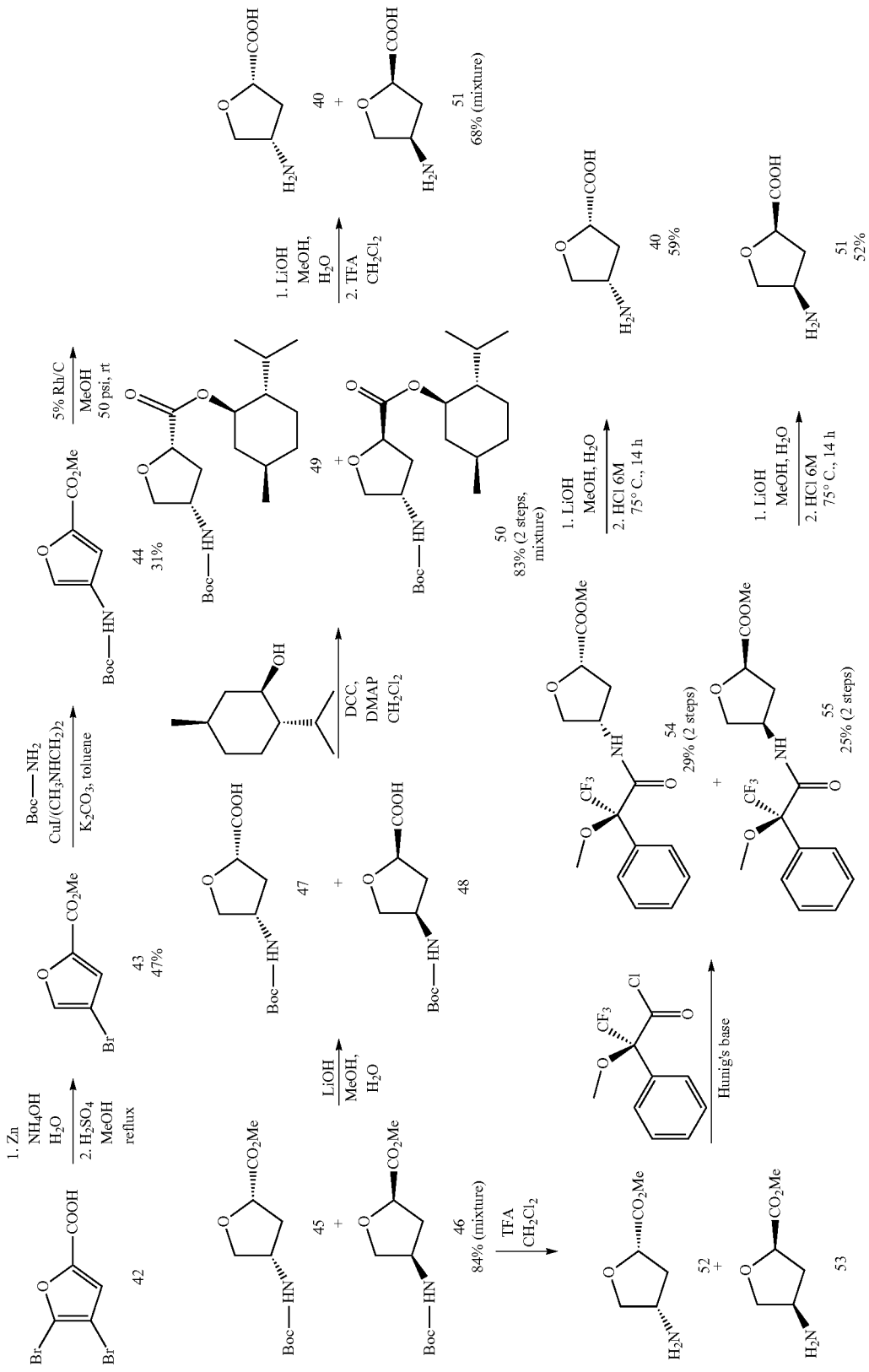

Compound 41 was synthesized, starting from commercially available 52 (Scheme 8). Surprisingly, the removal of the Fmoc group by piperidine in DMF at room temperature or at 50° C. was not successful, and 52 was recovered quantitatively. The Fmoc group, however, was successfully removed by diethylamine in acetonitrile. The Boc group was then removed by TFA in $CH_2Cl_2$. In a similar fashion, (2R,4S) tetrahydropyrrole analog 54 was synthesized from commercially available 53 (Scheme 8).

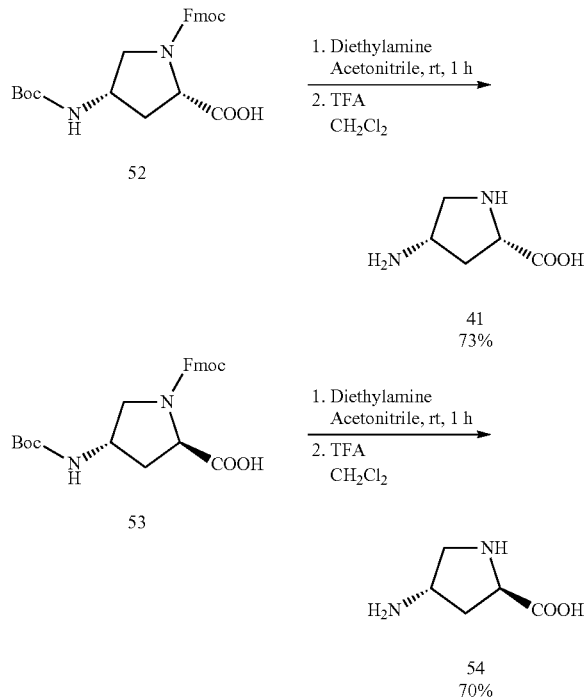

Preliminary results showed that the mixture of enantiomers 40 and 51 (Scheme 7) was a mixture of competitive inhibitors of GABA-AT with a $K_i$=0.43 mM. Preliminary results also showed that 41 (Scheme 8) was a competitive inhibitor of GABA-AT with a $K_i$=1.3 mM. These results further support the role of the sulfur atom in the PLP-17 adduct in retaining the product in the active site of GABA-AT, thereby inactivating the enzyme.

Compound 17 was also tested for the inhibition of hERG and microsomal cytochromes P450 (CYPs). hERG is a potassium ion channel that contributes to the electrical activity of the heart, which coordinates the heart's beating. This channel is sensitive to drug binding; therefore, when its ability to conduct electrical current across the cell membrane is compromised, it can result in potentially fatal cardiac adverse effects. The results showed that 17 did not inhibit the activity of the hERG channel (FIG. 9). CYPs are major enzymes that are involved in drug metabolism. They account for ~75% of all drug metabolism. Microsomal stability is often performed to predict if a drug will be eliminated too rapidly during drug development. The results showed that 17 did not inhibit or induce the seven most common CYPs (1A, 2B6, 2C8, 2C9, 2C19, 2D6, and 3A) that are involved in ~95% of the reactions in drug metabolism (FIG. 10).

Compound 17 was also evaluated for its plasma protein binding and its metabolic stability in human liver microsomes (HLM). The results showed that the plasma protein binding of 17 was only 26%, indicating a high percentage of free drug in plasma. Measurement of the metabolic stability in HLM was accomplished by incubating 17 with the microsomes and monitoring its disappearance with time using LC-MS/MS. Imipramine, propranolol, terfenadine, and verapamil were run in similar condition as controls. The results showed that 17 was metabolized less than 20% over 60 minutes in HLM (FIG. 11).

The present invention can also, as would be understood by those skilled in the art, be extended to or include methods using or in conjunction with a pharmaceutical composition comprising an inhibitor or inactivator compound of the sort described herein in a physiologically or otherwise suitable formulation. In some embodiments, the present invention includes one or more such compounds, as outlined above or discussed more fully below, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or non-aqueous solutions, dispersions, suspensions or emulsions. The resulting compositions can be, in conjunction with the various methods described herein, for administration or contact with a human/animal enzyme expressed or otherwise present therein. Whether or not in conjunction with a pharmaceutical composition, "contacting" means that a GABA aminotransferase and one or more inhibitor/inactivator compounds are brought together for purpose of binding and/or complexing such compound(s) to the enzyme. Amounts of one or more such compounds effective to affect or otherwise inhibit a GABA aminotransferase may be determined empirically, and making such determinations is within the skill in the art. Inhibition, inactivation, affecting or otherwise modulating GABA aminotransferase activity includes both reduction and/or mitigation, as well as elimination of GABA-AT activity and/or glutamate production.

It is understood by those skilled in the art that dosage amount will vary with the activity of a particular inhibitor/inactivator compound, disease state, route of administration, duration of treatment and like factors well-known in the medical and pharmaceutical arts. In general, a suitable dose will be an amount which is the lowest dose effective to produce a therapeutic or prophylactic effect. If desired, an effective dose of such a compound, pharmaceutically acceptable salt thereof or related composition may be administered in two or more sub-doses, administered separately over an appropriate period of time.

Methods of preparing pharmaceutical formulations or compositions include the step of bringing an inhibitor/inactivator compound into association with a carrier and, optionally, one or more additional adjuvants or ingredients. For example, standard pharmaceutical formulation techniques can be employed, such as those described in Remington's Pharmaceutical Sciences, Mac Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more inhibitor compounds for the manufacture of a medicament for therapeutic use in the treatment or prevention of disease states indicated by high GABA-AT activity, low GABA levels, and/or associated excessive neuronal activity.

EXAMPLES OF THE INVENTION

The following non-limiting examples and data illustrate various aspects and features relating to the compounds, compositions and/or methods of the present invention, including the preparation of various small molecule GABA-AT inactivator compounds, as are available through the synthetic methodologies described herein. In comparison with the prior art, the present compounds, compositions and methods provide results and data which are surprising, unexpected and contrary thereto. While the utility of this invention is illustrated through the use of several compounds, structural features and moieties thereof, it will be understood by those skilled in the art that comparable results are obtainable with various other compounds, structural features and moieties thereof, as are commensurate with the scope of this invention.

General Procedures

Chemicals were obtained from TCI America, Sigma-Aldrich, Alfa Aesar, and American Radiolabeled Chemicals, and used as received unless specified. All syntheses were conducted under anhydrous conditions in an atmosphere of argon, using flame-dried apparatus and employing standard techniques in handling air-sensitive materials, unless otherwise noted. All solvents were distilled and stored under an argon or nitrogen atmosphere before use. $^1$H NMR and $^{13}$C NMR spectra were taken on a Bruker AVANCE III 500 spectrometer using $CDCl_3$, MeOD, $(CD_3)_2CO$, or $D_2O$ as solvents, recorded in δ (ppm) and referenced to $CDCl_3$ (7.26 ppm for $^1$H NMR and 77.16 ppm for $^{13}$C NMR) or MeOD (3.31 ppm for 1H NMR and 49.00 ppm for $^{13}$C NMR) or $(CD_3)_2CO$ (2.05 ppm for 1H NMR and 29.84 ppm for $^{13}$C NMR) or $D_2O$ (4.79 ppm for $^1$H NMR). Nuclear Overhauser Effect (NOE) correlation experiments were performed using an Agilent $DDR_2$ 400 MHz spectrometer. High resolution mass spectra (HRMS) were measured with an Agilent 6210 LC-TOF (ESI, APCI, APPI) mass spectrometer. The purity of the synthesized final compounds was determined by HPLC analysis to be >95%. The column used was a Chiralcel OD-H 5 μm, 4.6×250 mm. After thorough column equilibration, compounds were eluted with a mobile phase of 2% EtOH in hexanes at 0.6 mL/min. Biochemical assays were performed using a Biotek Synergy H1 microplate reader. Prior to their evaluation, initial experiments were performed to confirm the synthesized analogues do not inhibit the coupling enzymes utilized in the substrate and inhibition assays. Metabolomics: LC gradient was employed at a flow rate of 200 μL/min on an Agilent 1150 LC system (Agilent, Santa Clara, Calif., USA); mass spectrometry was performed on a Q-Exactive mass spectrometer (Thermo Fisher Scientific, Waltham, Mass., USA). Crystallographic data were collected on beamlines 23ID-B and 23ID-D of GM/CA@APS of the Advanced Photon Source (APS) using X-rays of 0.99 Å wavelength and Rayonix (formerly MAR-USA) 4×4 tiled CCD detector with a 300 mm$^2$ sensitive area.

Example 1

(S)-Methyl 2-((tert-butoxycarbonyl)amino)-3-((2-methoxy-2-oxoethyl)thio)propanoate (24)

To a stirred light suspension of D-cysteine methyl ester hydrochloride (23, 5 g, 29.1 mmol) and $Boc_2O$ (7 mL, 30.6 mmol) in anhydrous $CH_2Cl_2$ (250 mL) at 0° C. was added $Et_3N$ (15.4 mL, 111 mmol) over a 10 min period. After addition, the cooling bath was removed, and the reaction solution was stirred at rt overnight. After being cooled to 0° C., methyl bromoacetate (3.3 mL, 35 mmol) was added to the reaction solution and was stirred for 30 min before removal of the cooling bath. Stirring was continued for 2 h at rt, followed by removal of the bulk of the solvent under reduced pressure. The resulting crude mixture was diluted with ether (60 mL), washed with water (3×30 mL) and brine (5 mL), dried ($MgSO_4$), and concentrated. Chromatography (ethyl acetate/hexanes, 3:7) afforded the desired product as a clear oil (6.79 g, 74%). $^1$H NMR matched literature value. $^1$H NMR (500 MHz, $CDCl_3$) δ 5.40 (d, J=8.2 Hz, 1H), 4.55 (m, 1H), 3.75 (s, 3H), 3.73 (s, 3H), 3.26 (q, J=15.2 Hz, 2H), 3.07 (m, 2H), 1.43 (s, 9H). $^{13}$C NMR (126 MHz, $CDCl_3$) δ 171.50, 170.61, 155.27, 80.35, 53.16, 52.78, 52.66, 35.02, 33.90, 28.38. FIRMS (LC-TOF): Calculated for $C_{12}H_{21}NO_6S$ [M+Na]$^+$330.0982; found 330.1001.

Example 2

(3R,4S)-Methyl 4-((tert-butoxycarbonyl)amino)-3-methoxy-3-((trimethylsilyl)oxy)tetrahydrothiophene-2-carboxylate (26)

To a solution of 24 (6.59 g, 21.4 mmol) in anhydrous di-chloromethane (100 mL) at 0° C. was added $Et_3N$ (3.3 mL, 23.6 mmol) followed by dropwise addition of TMSOTf (4.25 mL, 23.5 mmol) over 20 min. The mixture was stirred for 10 min at 0° C. then allowed to warm to rt. After being quenched with saturated sodium bicarbonate (50 mL), the organic layer was separated and washed with saturated $NaHCO_3$ (2×50 mL), dried ($MgSO_4$) and concentrated to obtain crude intermediate 25.

In a separate flask, a solution of lithium tetramethylpiperidide was prepared by the dropwise addition of n-BuLi (14.0 mL, 22.4 mmol; 1.6 M solution in hexanes) to a solution of 2,2,6,6-tetramethylpiperidide (4.17 mL, 24.5 mmol) in THF (100 mL) at −78° C. After a brief warm-up to rt, the solution was cooled to −78° C., and crude intermediate 25 in THF (50 mL) was added dropwise over 30 min. After the addition, the reaction was stirred at −78° C. for 30 min and at −40° C. for another 30 min. The reaction was cooled again to −78° C. and quenched with acetic acid (3 mL). The reaction mixture was diluted in ether (100 mL), washed with water (3×100 mL), 0.5 N HCl (3×30 mL), and brine (10 mL), dried ($MgSO_4$), and concentrated. The crude product was purified by chromatography (ethyl acetate/hexanes, 3:17) to yield the major diastereomer (26) as a white solid (2.91 g, 36%). $^1$H NMR matched literature value. $^1$H NMR (500 MHz, $CDCl_3$) δ 6.76 (d, J=9.5 Hz, 1H), 4.22 (ddd, J=9.6, 5.1, 1.8 Hz, 1H), 4.06 (s, 1H), 3.70 (s, 3H), 3.31 (s, 3H), 3.23 (dd, J=10.9, 5.1 Hz, 1H), 2.80 (dd, J=10.9, 1.9 Hz, 1H), 1.40 (s, 9H), 0.11 (s, 9H). $^{13}$C NMR (126 MHz, $CDCl_3$) δ 173.09, 155.37, 110.31, 79.39, 59.44, 52.83, 50.78, 49.65, 36.83, 28.50, 0.89. FIRMS (LC-TOF): Calculated for $C_{15}H_{29}NO_6SSi$ [M+Na]$^+$402.1377; found 402.1388.

Example 3

(S)-Methyl 4-((tert-butoxycarbonyl)amino)-4,5-di-hydrothiophene-2-carboxylate (28)

To a stirred solution of 26 (979 mg, 2.58 mmol) in 1 M HF solution (13 mL, prepared by diluting 48% aqueous HF in dry methanol) at rt was added TBAF (2.84 mL, 2.84 mmol; 1 M solution in THF). The reaction was stirred at rt for 2 h before being cooled in an ice/brine bath. Once cooled, NaBH4 (199 mg, 5.16 mmol) was added in small portions while maintaining a reaction temp of 0° C. Following addition, the reaction was stirred for 1 h at 0° C. before being quenched with acetone (1.3 mL) and allowed to continue stirring at rt. After 1 h, acetic acid (161 µL) was added, followed by removal most of the solvent under reduced pressure. The resulting crude mixture was diluted with ethyl acetate (30 mL) and washed with 1:1 saturated brine:water (15 mL), water (2×15 mL), and brine (3 mL), dried ($MgSO_4$), and concentrated to yield the crude alcohol, which was used in the next step without purification.

To a stirred solution of the crude alcohol in $CH_2Cl_2$ (13 mL) at 0° C. was added $Et_3N$ (1.44 mL, 10.3 mmol), followed by mesyl chloride (400 µL, 5.17 mmol) dropwise. The reaction was stirred for 30 min at 0° C. and overnight at rt. After removal of most of the solvent under reduced pressure, the resulting crude mixture was diluted with ethyl ether (30 mL), washed with water (2×15 mL), 0.5 M HCl (15 mL), and brine (3 mL), dried ($MgSO_4$), and concentrated. Chromatography (ethyl acetate/hexanes, 3:7) afforded the desired product as a white solid (430 mg, 64%). $^1$H NMR (500 MHz, $CDCl_3$) δ 6.51 (d, J=3.3 Hz, 1H), 5.15 (m, 1H), 4.90 (d, J=9.2 Hz, 1H), 3.79 (s, 3H), 3.61 (dd, J=12.3, 8.3 Hz, 1H), 3.13 (dd, J=12.3, 4.2 Hz, 1H), 1.43 (s, 9H). $^{13}$C NMR (126 MHz, $CDCl_3$) δ 162.68, 154.74, 138.37, 131.93, 80.35, 58.29, 52.76, 39.40, 28.44. HRMS (LC-TOF): Calculated for $C_{11}H_{17}NO_4S$ $[M+Na]^+$ 282.0770; found 282.0773.

Example 4

(2S,4S)- and (2R,4S)-Methyl 4-((tert-butoxycarbonyl)amino)tetrahydrothiophene-2-carboxylate (29 and 30)

Magnesium turnings (484 mg, 19.9 mmol) were added to a mixture of (S)-methyl 4-((tert-butoxy carbonyl)amino)-4,5-dihydrothiophene-2-carboxylate (28, 430 mg, 1.66 mmol) and $NH_4Cl$ (5.33 g, 99.6 mmol) in MeOH (15 mL), and the resulting mixture was vigorously stirred overnight at rt. After removal of most of the solvent under reduced pressure, the resulting crude mixture was diluted with water (20 mL) and extracted with ethyl ether (3×40 mL). The combined organics were washed with brine (2 mL), dried ($MgSO_4$), and concentrated. Chromatography (ethyl ether/toluene, 2:8) afforded 29 (109 mg, 25%) and 30 (141 mg, 32%) as white solids. (29): $^1$H NMR (500 MHz, $CDCl_3$) δ 5.86 (d, J=7.6 Hz, 1H), 4.55-4.40 (m, 1H), 3.97 (dd, J=8.6, 3.1 Hz, 1H), 3.72 (s, 3H), 3.11 (dd, J=11.0, 5.0 Hz, 1H), 2.92 (dd, J=11.3, 3.6 Hz, 1H), 2.37-2.26 (m, 1H), 2.17 (ddd, J=14.0, 8.5, 6.0 Hz, 1H), 1.41 (s, 9H); $^{13}$C NMR (126 MHz, $CDCl_3$) δ 175.10, 155.31, 79.48, 55.54, 52.95, 45.68, 40.16, 37.28, 28.48; HRMS (LC-TOF): Calculated for $C_{11}H_{19}NO_4S$ $[M+Na]^+$ 284.0927, found 284.0931. (30): $^1$H NMR (500 MHz, $(CD_3)_2CO$) δ 6.25 (d, J=3.4 Hz, 1H), 4.49 (tt, J=7.4, 3.8 Hz, 1H), 4.06 (dd, J=7.5, 5.1 Hz, 1H), 3.69 (s, 3H), 3.14 (dd, J=10.5, 5.6 Hz, 1H), 2.78 (dd, J=10.5, 6.2 Hz, 1H), 2.42 (dt, J=13.0, 5.3 Hz, 1H), 2.15-2.05 (m, 1H), 1.42 (s, 9H); $^{13}$C NMR (126 MHz, $(CD_3)_2CO$) δ 174.00, 155.92, 78.96, 55.98, 52.52, 44.49, 37.69, 37.53, 28.53; HRMS (LC-TOF): Calculated for $C_{11}H_{19}NO_4S$ $[M+Na]^+$ 284.0927, found 284.0931.

Example 5

(2S,4S)-4-Aminotetrahydrothiophene-2-carboxylic acid hydrochloride (17)

Boc-protected amino acid ester 29 (100 mg, 0.38 mmol) was dissolved in 4 N HCl (5 mL) and acetic acid (5 mL). The resulting solution was heated to 70° C. and stirred for 5 h before being concentrated in vacuo to afford a solid. The solid was purified by ion-exchange chromatography (AG 50W-X8), eluting with a gradient from 0.4 N to 2.0 N HCl, giving the desired amino acid hydrochloride product as a white solid (63 mg, 89%). $^1$H NMR (500 MHz, MeOD) δ 4.10 (m, 2H), 3.32 (dd, J=11.8, 5.6 Hz, 1H), 3.09 (dd, J=11.8, 5.0 Hz, 1H), 2.52-2.43 (m, 1H). $^{13}$C NMR (126 MHz, MeOD) δ 177.11, 55.99, 46.14, 37.28, 36.77. FIRMS (LC-TOF): Calculated for $C_5H_9NO_2S$ $[M-H]^-$ 146.0281; found 146.0278.

Example 6

(2R,4S)-4-Aminotetrahydrothiophene-2-carboxylic acid hydrochloride (18)

Compound 18 (61 mg, 87%) was synthesized from 30 (100 mg, 0.38 mmol) using a similar procedure to that for 17 from 29. $^1$H NMR (500 MHz, MeOD) δ 4.15 (p, J=5.9 Hz, 1H), 4.05 (dd, J=7.6, 4.5 Hz, 1H), 3.28 (dd, J=11.6, 5.7 Hz, 1H), 2.95 (dd, J=11.5, 5.7 Hz, 1H), 2.65 (dt, J=13.6, 5.0 Hz, 1H), 2.18 (dt, J=13.9, 7.2 Hz, 1H). $^{13}$C NMR (126 MHz, MeOD) δ 175.62, 55.75, 45.19, 37.22, 35.81. HRMS (LC-TOF): Calculated for $C_5H_9NO_2S$ $[M-H]^-$ 146.0281; found 146.0278.

Example 7

(4S)-Methyl 4-((tert-butoxycarbonyl)amino)tetrahydrothiophene-2-carboxylate 1,1-dioxide (31)

To a stirred solution of 29 (60 mg, 0.23 mmol) and $MnSO_4·H_2O$ (1 mg) in $CH_3CN$ (5 mL) was added at room temperature a mixture of 30% $H_2O_2$ (1.15 mmol, 118 µL) and 0.2 M $NaHCO_3$ (3.4 mL), previously prepared at 0° C. After 15 min the reaction was quenched with brine, extracted with ethyl acetate (3×10 mL), dried ($Na_2SO_4$), and concentrated. Chromatography (ethyl acetate/hexanes; 1:9) provided the desired product as a 1:1 mixture of the two diastereomers (55 mg, 81%). $^1$H NMR (500 MHz, $CDCl_3$) δ [5.57 (d, J=7.1 Hz); 5.21 (d, J=6.2 Hz), 1H], [4.65 (br s), 4.54 (sex, J=6.6 Hz), 1H], [4.14 (t, J=7.9 Hz), 4.11 (dd, J=9.1, 6.1 Hz), 1H], [3.88 (s), 3.85 (s), 3H], [3.47 (dd, J=13.5, 6.9 Hz), 3.42 (dd, J=13.7, 7.0 Hz), 1H], [3.18 (t, J=4.9 Hz), 3.15 (t, J=5.4 Hz), 1H], [2.83 (dt, J=13.9, 6.8 Hz), 2.69 (ddd, J=14.1, 8.9, 6.9 Hz), 1H], 2.50 (m, 1H), 1.44 (s, 9H). $^{13}$C NMR (126 MHz, $CDCl_3$) δ [166.49, 165.77], [155.00, 154.78], [80.76, 80.59], [65.14, 64.02], [57.07, 56.05], [53.98, 53.78], [45.54, 45.37], [33.30, 32.23], [28.43, 28.41]. HRMS (LC-TOF): Calculated for $C_{11}H_{19}NO_6S$ $[M+Na]^+$ 316.0825; found 316.0833.

Example 8

(4S)-4-Aminotetrahydrothiophene-2-carboxylic acid 1,1-dioxide hydrochloride (19)

Compound 19 was synthesized from 31 as an inseparable 1:1 mixture of diastereomers using a procedure similar to that for 17 from 29 (86%). $^1$H NMR (500 MHz, MeOD) δ [4.41 (dd, J=8.6, 4.9 Hz), 4.36 (dd, J=9.5, 7.9 Hz), 1H], [4.27 (p, J=7.4 Hz), 4.12 (p, J=8.1 Hz), 1H], [3.73 (dd, J=13.8, 8.1 Hz), 3.68 (dd, J=13.8, 8.0 Hz), 1H], [3.35 (dd, J=13.9, 7.1 Hz), 3.29 (dd, J=13.5, 8.1 Hz), 1H], [2.96 (ddd, J=14.2, 7.0, 5.0 Hz), 2.84 (dt, J=14.2, 7.2 Hz), 1H], [2.55 (dt, J=13.9, 9.3 Hz), 2.46 (dt, J=14.3, 8.1 Hz), 1H]. $^{13}$C NMR (126 MHz, MeOD) δ [167.13, 167.04], [66.52, 65.56], [54.61, 54.44], [46.38, 45.40], [31.40, 31.37]. HRMS (LC-TOF): Calculated for $C_5H_9NO_4S$ [M+Na]$^+$202.0144; found 202.014.

Example 9

(1R,4S)-2-azabicyclo[2.2.1]heptan-3-one (38)

Compound 38 was prepared from (1S,4R)-2-azabicyclo [2.2.1]hept-5-en-3-one (37) by following a published procedure (94%). (Evans, C.; McCague, R.; Roberts, S. M.; Sutherland, A. G. *J. Chem. Soc., Perkin Trans.* 1 1991, 656-657.) $^1$H NMR matched literature value. $^1$H NMR (500 MHz, CDCl$_3$) δ 5.53 (br s, 1H), 3.90 (m, 1H), 2.76 (m, 1H), 1.95-1.40 (m, 6H). $^{13}$C NMR (126 MHz, CDCl$_3$) δ 181.05, 55.54, 45.04, 41.37, 30.34, 23.79. HRMS (LC-TOF): Calculated for $C_6H_9NO$ [M+Na]$^+$134.0576; found 134.0578.

Example 10

Preparation of (1S,3R)-3-aminocyclopentane-1-carboxylic acid (39)

Compound 39 was prepared from 38 by following a published procedure (80%). (Forró, E.; Fülöp, F. *Eur. J. Org. Chem.* 2008, 2008, 5263-5268.) $^1$H NMR matched literature value. $^1$H NMR (500 MHz, D$_2$O) δ 3.76 (m, 1H), 3.01 (m, 1H), 2.44-1.79 (m, 6H). $^{13}$C NMR (126 MHz, D$_2$O) δ 180.01, 51.47, 42.40, 33.65, 29.81, 27.68. HRMS (LC-TOF): Calculated for $C_6H_{11}NO_2$ [M+H]$^+$ 130.0863; found 130.0864.

Example 11

Preparation of methyl 4-bromofuran-2-carboxylate (43)

4,5-Dibromo-2-furoic acid (7.5 g, 27.8 mmol) was suspended in water (83 mL) and saturated NH$_4$OH (27 mL) with vigorous stirring at room temperature. Zinc dust (<10 micron, 1.82 g, 27.8 mmol) was added, and the mixture was stirred at r.t. for 3 h. The reaction mixture was filtered through a pad of Celite and then acidified with 2N HCl to pH 2. The filtrate was extracted with ethyl acetate (4×200 mL), combined, dried (Na$_2$SO$_4$), and concentrated to afford 3.47 g of white solids. This crude intermediate was dissolved in methanol (90 mL), and concentrated sulfuric acid (0.6 mL) was then added while stirring. The resulting solution was heated to reflux and stirred overnight. The reaction mixture was then cooled to r.t. and concentrated. Saturated NaHCO$_3$ (50 mL) was added, the resulting suspension was extracted with ethyl ether (4×50 mL). The organic layers were combined, washed with brine (5 mL), dried with MgSO$_4$, filtered, and concentrated to afford 3.26 g of yellow solids, which was then recrystallized with hexanes (5 mL) to afford 43 as a white solid (2.69 g, 72%). $^1$H NMR and $^{13}$C NMR matched literature values. $^1$H NMR (500 MHz, CDCl$_3$) δ 7.57 (d, J=1.0 Hz, 1H), 7.18 (d, J=1.0 Hz, 1H), 3.90 (s, 3H). $^{13}$C NMR (126 MHz, CDCl$_3$) δ 158.32, 145.13, 144.56, 120.45, 101.41, 52.39. HRMS (LC-ESI): Calculated for $C_6H_6BrO_3$ [M+H]$^+$ 204.9495, found 204.9486.

Example 12

Preparation of methyl 4-((tert-butoxycarbonyl)amino)furan-2-carboxylate (44)

tert-Butyl carbamate (1.87 g, 15.7 mmol) and a stir bar were added to an oven-dried sealable vial (10-20 mL). Potassium carbonate (4.53 g, 32.8 mmol), CuI (749 mg, 3.93 mmol), and 43 (2.69 g, 13.1 mmol) were added to the vial. A septum was put on the vial, and the system was put under reduced pressure and back-filled with nitrogen twice. Toluene (10 mL) and N,N'-dimethylethylenediamine (427 µL, 3.93 mmol) were added via syringes. The septum was removed, and the vial was quickly sealed. The resulting mixture was stirred at 110° C. for 21 h. The reaction mixture was cooled to r.t., filtered through a pad of silica gel, and eluted with a mixture of CH$_2$Cl$_2$ and ethyl acetate (1:1, 80 mL). The organic solution was then concentrated. Chromatography (ethyl acetate/hexanes; 3:7) provided 44 as a white solid (988 mg, 31%). $^1$H NMR and $^{13}$C NMR matched literature values. $^1$H NMR (500 MHz, CDCl$_3$) δ 7.89 (s, 1H), 7.00 (s, 1H), 6.30 (br s, 1H), 3.88 (s, 3H), 1.50 (s, 9H). $^{13}$C NMR (126 MHz, CDCl$_3$) δ 159.05, 152.61, 142.87, 134.52, 126.59, 111.35, 81.32, 52.17, 28.40. HRMS (LC-ESI): Calculated for $C_{11}H_{15}NNaO_5$ [M+Na]$^+$264.0842, found 264.0840.

Example 13

Preparation of the mixture of methyl (2S,4S)-4-((tert-butoxycarbonyl)amino)tetrahydrofuran-2-carboxylate (45) and methyl (2R,4R)-4-((tert-butoxycarbonyl)amino)tetrahydrofuran-2-carboxylate (46)

Rhodium on carbon (dry basis, 5 wt %, 98.5 mg) was added to a Parr bottle (500 mL). 44 (985 mg, 4.08 mmol) was dissolved in dry methanol (40 mL) and pipetted into the Parr bottle. The Parr bottle was sealed and put under hydrogen at 37 psi. The Parr bottle was shaken at r.t. for 48 h. The reaction mixture was filtered through a pad of Celite and washed with methanol (2×30 mL). The filtrate was concentrated. Chromatography (ethyl acetate/hexanes; 4:6) provided a mixture of 45 and 46 as a white solid (845 mg, 84%). $^1$H NMR and $^{13}$C NMR matched literature values. $^1$H NMR (500 MHz, CDCl$_3$) δ 5.15 (br s, 1H), 4.50 (dd, $J_1$=9.4 Hz, $J_2$=4.1 Hz, 1H), 4.35 (br s, 1H), 3.99 (dd, $J_1$=9.4 Hz, $J_2$=5.3 Hz, 1H), 3.89 (br d, J=9.7 Hz, 1H), 3.78 (s, 3H), 2.52 (m, 1H), 2.01 (dt, $J_1$=13.8 Hz, $J_2$=3.4 Hz, 1H), 1.43 (s, 9H). $^{13}$C NMR (126 MHz, CDCl$_3$) δ 173.86, 155.40, 79.81, 76.13, 75.13, 52.54, 51.10, 37.17, 28.51. HRMS (LC-ESI): Calculated for $C_{11}H_{19}NNaO_5$ [M+Na]$^+$268.1155, found 268.1154.

Example 14

Preparation of the mixture of (1R,2S,5R)-2-isopropyl-5-methylcyclohexyl (2S,4S)-4-((tert-butoxycarbonyl)amino)tetrahydrofuran-2-carboxylate (49) and (1R,2S,5R)-2-isopropyl-5-methylcyclohexyl (2R,4R)-4-((tert-butoxycarbonyl)amino)tetrahydrofuran-2-carboxylate (50)

A mixture of 45 and 46 (451 mg, 1.84 mmol) was dissolved in methanol (7.5 mL), and a solution of LiOH (133 mg, 5.55 mmol, in 2.5 mL water) was added. The resulting solution was stirred at r.t. overnight. The reaction mixture was concentrated, and the resulting white solid was dissolved in water (40 mL). The aqueous solution was washed with ethyl ether (3×20 mL), acidified with 2N HCl to pH 1, and then extracted with ethyl acetate (3×40 mL). The ethyl acetate solution was washed with brine (5 mL), dried with MgSO$_4$, filtered, and concentrated to afford a light yellow oil (381 mg). This crude oil was dissolved in CH$_2$Cl$_2$ (6 mL), and (1R,2S,5R)-(−)-menthol (258 mg, 1.65 mmol) and 4-(dimethylamino)pyridine (20.2 mg, 0.165 mmol) were added. The resulting solution was cooled to 0° C., and DCC (340 mg, 1.65 mmol) was added. The reaction solution was stirred at 0° C. for 5 min and then at r.t. for 4 h. The reaction mixture was filtered through a pad of Celite, and the filtrate was concentrated. The resulting residue was dissolved in CH$_2$Cl$_2$, washed with 0.5N HCl (2×30 mL), saturated NaHCO$_3$ (30 mL), and brine (5 mL), and dried with MgSO$_4$, filtered, and concentrated. Chromatography (ethyl acetate/hexanes; 2:8) provided a mixture of 49 and 50 as a clear gel (508 mg, 83%). $^1$H NMR and $^{13}$C NMR showed a mixture of 49 and 50 (1:1 ratio). HRMS (LC-ESI): Calculated for C$_{20}$H$_{35}$NNaO$_5$ [M+Na]$^+$392.2407, found 392.2409.

Example 15

Preparation of the mixture of (2S,4S)-4-aminotetrahydrofuran-2-carboxylic acid (40) and (2R,4R)-4-aminotetrahydrofuran-2-carboxylic acid (51)

A mixture of 49 and 50 (490 mg, 1.33 mmol) was dissolved in methanol (7.5 mL), and a solution of LiOH (95.6 mg, 3.99 mmol, in 2.5 mL water) was added. The resulting solution was stirred at r.t. overnight. The reaction mixture was concentrated, and the resulting white solid was dissolved in water (30 mL). The aqueous solution was washed with ethyl ether (3×30 mL), acidified with 2N HCl to pH 1, and then extracted with ethyl acetate (3×50 mL). The ethyl acetate solution was washed with brine (5 mL), dried with MgSO$_4$, filtered, and concentrated to afford a white solid (307 mg). The crude solid was dissolved in dry CH$_2$Cl$_2$ (7 mL), and trifluoroacetic acid (2 mL) was added dropwise over 10 min. The resulting solution was stirred at r.t. for 1 h. The reaction mixture was concentrated and purified through HPLC using a C18 column to afford a mixture of enantiomers 40 and 51 as a white solid (119 mg, 68%). $^1$H NMR (500 MHz, MeOD) δ 4.49 (m, 1H), 4.01 (m, 2H), 3.96 (m, 1H), 2.74 (m, 1H), 2.10 (m, 1H). $^{13}$C NMR (126 MHz, MeOD) δ 175.55, 77.41, 72.56, 52.26, 35.34. 1D NOE (not shown) confirmed that the carboxylic group and the amino group were on same side of the tetrahydrofuran ring.

Example 16

Preparation of methyl (2S,4S)-4-((R)-3,3,3-trifluoro-2-methoxy-2-phenylpropanamido)tetrahydrofuran-2-carboxylate (54) and methyl (2R,4R)-4-((R)-3,3,3-trifluoro-2-methoxy-2-phenylpropanamido)tetrahydrofuran-2-carboxylate (55)

A mixture of 45 and 46 (82 mg, 0.33 mmol) was dissolved in dry CH$_2$Cl$_2$ (10 mL), and trifluoroacetic acid (2.5 mL) was added dropwise over 10 min. The resulting solution was stirred at r.t. for 1 h. The reaction mixture was concentrated and dried under high vacuum overnight. The crude residue was dissolved in dry CH$_2$Cl$_2$ (10 mL) and cooled to 0° C. Diisopropylethylamine (288 µL, 1.65 mmol) and (S)-(+)-Mosher acid chloride (94 µL, 0.50 mmol) were added. The resulting mixture was stirred at r.t. for 1 h and then concentrated. Chromatography (ethyl acetate/hexanes; 4:6) provided a mixture of 54 and 55 as a white solid (108 mg, 91%). Separation of these two diastereomers was carried out by the Northwestern University Center for Molecular Innovation and Drug Discovery using HPLC with a semi-prep Whelk-01 chiral column. 54 was obtained as a clear oil (35 mg, 29%), and 55 was obtained as a clear oil (30 mg, 25%). Compound 54: $^1$H NMR (500 MHz, CDCl$_3$) δ 7.67 (d, J=8.0 Hz, 1H), 7.50 (m, 2H), 7.41 (m, 3H), 4.71 (m, 1H), 4.57 (dd, J$_1$=9.7 Hz, J$_2$=3.2 Hz, 1H), 4.03 (dd, J$_1$=9.5 Hz, J$_2$=5.0 Hz, 1H), 3.95 (dt, J$_1$=9.3 Hz, J$_2$=1.6 Hz, 1H), 3.78 (s, 3H), 3.37 (q, J=1.5 Hz, 3H), 2.58 (dq, J$_1$=9.7 Hz, J$_2$=7.0 Hz, 1H), 2.10 (dquint, J$_1$=13.9 Hz, J$_2$=1.2 Hz, 1H). $^{13}$C NMR (126 MHz, CDCl$_3$) δ 173.79, 166.14, 132.22, 129.68, 128.81, 127.87, 125.08, 122.82, 76.18, 74.84, 55.00, 52.60, 49.90, 37.30. HRMS (LC-ESI): Calculated for C$_{16}$H$_{18}$F$_3$NNaO$_5$ [M+Na]$^+$ 384.1029, found 384.1033. Compound 55: $^1$H NMR (500 MHz, CDCl$_3$) δ 7.55 (d, J=8.3 Hz, 1H), 7.51 (m, 2H), 7.40 (m, 3H), 4.70 (m, 1H), 4.54 (dd, J$_1$=9.6 Hz, J$_2$=3.2 Hz, 1H), 4.05 (dd, J$_1$=9.7 Hz, J$_2$=4.8 Hz, 1H), 4.01 (dq, =9.5 Hz, J$_2$=1.2 Hz, 1H), 3.65 (s, 3H), 3.44 (q, J=1.6 Hz, 3H), 2.52 (dq, =9.6 Hz, J$_2$=6.9 Hz, 1H), 1.99 (dquint, J$_1$=13.8 Hz, J$_2$=1.2 Hz, 1H). $^{13}$C NMR (126 MHz, CDCl$_3$) δ 173.73, 166.15, 132.73, 129.60, 128.70, 127.62, 124.97, 122.67, 76.15, 75.00, 55.13, 52.51, 49.95, 36.99. HRMS (LC-ESI): Calculated for C$_{16}$H$_{18}$F$_3$NNaO$_5$ [M+Na]$^+$384.1029, found 384.1032.

Example 17

Preparation of (2S,4S)-4-aminotetrahydrofuran-2-carboxylic acid (40)

54 (14 mg, 0.039 mmol) was dissolved in methanol (1.5 mL), and a solution of LiOH (4.7 mg, 0.20 mmol, in 0.5 mL water) was added. The resulting solution was stirred at r.t. overnight. The reaction mixture was concentrated, and the resulting white solid was dissolved in water (4 mL). The aqueous solution was washed with ethyl ether (4×4 mL), acidified with 2N HCl to pH 1, and then extracted with ethyl acetate (4×7 mL). The ethyl acetate solution was washed with brine (2 mL), dried with MgSO$_4$, filtered, and concentrated to afford a clear oil. The crude oil was dissolved in 6N HCl (3 mL), and the resulting solution was stirred at 75° C. for 14 h. The reaction mixture was concentrated and purified by ion-exchange chromatography (AG 50W-X8), eluting with 2.0 N HCl, and then by HPLC using a C18 column, affording 40 as a white solid (3 mg, 59%).

Example 18

Preparation of (2R,4R)-4-aminotetrahydrofuran-2-carboxylic acid (51)

55 (16 mg, 0.044 mmol) was dissolved in methanol (1.5 mL), and a solution of LiOH (5.3 mg, 0.22 mmol, in 0.5 mL water) was added. The resulting solution was stirred at r.t. overnight. The reaction mixture was concentrated, and the resulting white solid was dissolved in water (4 mL). The aqueous solution was washed with ethyl ether (4×4 mL), acidified with 2N HCl to pH 1, and then extracted with ethyl acetate (4×7 mL). The ethyl acetate solution was washed with brine (2 mL), dried with $MgSO_4$, filtered, and concentrated to afford a clear oil. The crude oil was dissolved in 6N HCl (3 mL), and the resulting solution was stirred at 75° C. for 14 h. The reaction mixture was concentrated and purified by ion-exchange chromatography (AG 50W-X8), eluting with 2.0 N HCl, and then by HPLC using a C18 column, affording 51 as a white solid (3 mg, 52%). HRMS (LC-APPI): Calculated for $C_5H_{10}NO_3$ $[M+H]^+$ 132.0655, found 132.0658.

Example 19

Preparation of (2S,4S)-4-aminopyrrolidine-2-carboxylic acid (41)

(2S,4S)-Boc-4-amino-1-fmoc-pyrrolidine-2-caboxylic acid (52) (232 mg, 0.51 mmol) was dissolved in acetonitrile (10 mL), and diethylamine (10 mL) was added dropwise. The resulting solution was stirred at r.t. for an hour and then concentrated. The crude solid was dissolved in dry $CH_2Cl_2$ (7 mL), and trifluoroacetic acid (2 mL) was added dropwise over 10 min. The resulting solution was stirred at r.t. for 2 h. The reaction mixture was concentrated and purified by ion-exchange chromatography (AG 50W-X8), eluting with 2.0 N HCl, and then by HPLC using a C18 column, affording 41 as a white solid (48 mg, 73%). $^1$H NMR (500 MHz, $D_2O$) δ 4.47 (t, J=8.8 Hz, 1H), 4.23 (quint, J=7.8 Hz, 1H), 3.88 (dd, =12.9 Hz, $J_2$=7.9 Hz, 1H), 3.59 (dd, =12.9 Hz, $J_2$=7.0 Hz, 1H), 2.99 (dt, $J_1$=14.0 Hz, $J_2$=8.1 Hz, 1H), 2.27 (dt, $J_1$=13.8 Hz, $J_2$=8.9 Hz, 1H). $^{13}$C NMR (126 MHz, $D_2O$) δ 171.24, 59.55, 48.33, 47.43, 32.14. FIRMS (LC-ESI): Calculated for $C_5H_{11}N_2O_2$ $[M+H]^+$ 131.0815, found 131.0809.

Example 20

Preparation of (2R,4S)-4-aminopyrrolidine-2-carboxylic acid (54)

(2R,4S)-Boc-4-amino-1-Fmoc-pyrrolidine-2-caboxylic acid (53) (250 mg, 0.55 mmol) was dissolved in acetonitrile (10 mL), and diethylamine (10 mL) was added dropwise. The resulting solution was stirred at r.t. for an hour and then concentrated. The crude solid was dissolved in dry $CH_2Cl_2$ (7 mL), and trifluoroacetic acid (2 mL) was added dropwise over 10 min. The resulting solution was stirred at r.t. for 2 h. The reaction mixture was concentrated and purified by ion-exchange chromatography (AG 50W-X8), eluting with 2.0 N HCl, and then by HPLC using a C18 column, affording 54 as a light yellow solid (50 mg, 70%). HRMS (LC-ESI): Calculated for $C_5H_{11}N_2O_2$ $[M+H]^+$ 131.0815, found 131.0816. Calculated for $C_5H_{10}N_2NaO_2$ $[M+Na]^+$ 153.0634, found 153.0636.

Example 21

Purification of GABA Aminotransferase (GABA-AT) from Pig Brain

GABA-AT was isolated and purified from pig brain by a published procedure. (Koo, Y. K.; Nandi, D.; Silverman, R. B. Arch. Biochem. Biophys. 2000, 374, 248-254.) The purified GABA-AT used in these experiments was found to have a concentration of 6.41 mg/mL with a specific activity of 1.84 units/mg.

Example 22

Evaluation of Compounds as Time-Dependent Inhibitors of GABA-AT

GABA-AT (17.5 μL) was incubated in the presence of varying concentrations of each compound (70 μL final volume) at 25° C. in 50 mM potassium pyrophosphate buffer solution, pH 6.5, containing 5 mM α-ketoglutarate and 1 mM β-mercaptoethanol. Aliquots (10 μL) were withdrawn at timed intervals and were added immediately to the assay solution (137 μL, see below) followed by the addition of SSDH (3 μL). The relative enzyme activity was determined by normalizing the rate of increasing absorbance at 340 nm to a control. A Kitz and Wilson replot was used to determine the kinetic constants $K_1$ and $k_{inact}$.

Example 23

Evaluation of Compounds as Inhibitors of GABA-AT

Inhibition constants were determined by monitoring GABA-AT activity in the presence of 0-50 mM concentrations of synthesized analogues using a coupled assay with the enzyme succinic semialdehyde dehydrogenase (SSDH). The assay solution consisted of 10 mM GABA, 5 mM α ketoglutarate, 1 mM $NADP^+$, 5 mM β-mercaptoethanol, and excess SSDH in 50 mM potassium pyrophosphate buffer, pH 8.5. Enzyme activity was determined by observing the change in absorbance at 340 nm at 25° C. $IC_{50}$ values were obtained using non-linear regression in GraphPad Prism5 software. Subsequent $K_i$ values were determined using the Cheng-Prusoff relationship. (Yung-Chi, C.; Prusoff, W. H. *Biochem. Pharmacol.* 1973, 22, 3099-3108.)

Example 24

Evaluation of Compounds as Substrates for GABA-AT

Compounds were tested using an experiment in which the conversion of α-ketoglutarate to L-glutamic acid was monitored as an indication of the rate of PLP reduction to PMP, which in turn corresponds to amine oxidation to the corresponding aldehyde. Enzyme reactions were prepared at 5 mM concentrations of compounds in 100 μL pyrophosphate buffer (50 mM, pH 8.5) containing 5 mM α-ketoglutarate and 0.13 mg/mL purified GABA-AT and allowed to incubate at room temperature for 24 h. The L-glutamic acid content was determined by combining 50 μL of each incubation mixture with 50 μL of Tris-HCl buffer (100 mM, pH 7.5) containing 100 μM Ampliflu™ Red (Sigma-Aldrich), 0.25 units/mL horseradish peroxidase and 0.08 units/mL L-glutamate oxidase in a 96-well black walled plate. After incubation at 37° C. for 30 min fluorescence was recorded with the aid of a microplate reader (BioTek Synergy H1) with 530 nm excitation and 590 nm emission wavelengths, where fluorescence is proportional to the L-glutamate concentration.

Example 25

Preparation of [7-$^3$H]-Pyridoxal 5'-Phosphate ([7-3H]PLP)

To a solution of pyridoxal 5'-phosphate (PLP) in water (1.8 mL, 0.28 M) was added thirty drops of 1 M NaOH. The mixture was then cooled to 0° C. in an ice bath, and a solution of NaBH$_4$ (5.86 mg, 0.15 mmol) and NaB[$^3$H]$_4$ (100 mCi) in 450 μL of 0.1 M NaOH was added in small portions and stirred for 1 h at 0° C. Concentrated HCl (120 μL) was then added to the solution very slowly (the pH of the resulting solution was 4), and the reaction was stirred for 5 min at 0° C. Ground MnO$_2$ (200 mg, 2.3 mmol) was added, and the resulting mixture was stirred for 2 h at rt. A solution of 1 M NaOH was added dropwise to bring the pH to 8, and the resulting solution was centrifuged. The supernatants were collected and loaded onto a gel filtration column packed with Bio-Rad AG1-X8 resin (hydroxide form). Water and 5 M acetic acid was used as the mobile phase (gradient from 90% water to 0% water, 1.5 mL/min, 300 min). Fractions (10 mL each) were collected and tested for UV absorption and radioactivity. The fractions with the desired product were lyophilized and then loaded onto an HPLC with a Phenomenex Gemini C18 column (4.6 mm×250 mm, 5μ, 110 Å). Water (with 0.1% TFA) and acetonitrile (with 0.1% TFA) were used as the mobile phase (5% acetonitrile, 0.5 mL/min, 25 min; then gradient to 95% acetonitrile, 0.5 mL/min, 20 min). Under these conditions, PLP eluted at 38 min. Fractions running with the PLP peak were collected, counted for radioactivity using liquid scintillation counting, and then lyophilized, affording [7-$^3$H] PLP.

Example 26

Preparation of [7-$^3$H]PLP-Reconstituted GABA-AT

To potassium phosphate buffer (0.5 mL, 100 mM, pH 7.4) containing β-mercaptoethanol (0.25 mM) (buffer A) and GABA-AT (170 μg, 1.55 nmol) protected from light was added GABA (10 mg, 0.097 mmol). The resulting solution was stirred at rt for 1 h and then was dialyzed at 4° C. against potassium phosphate buffer (200 mL, 500 mM, pH 5.5) containing β-mercaptoethanol (0.25 mM) (buffer B) and GABA (4.0 g, 39 mmol) for 3 h. The solution was then dialyzed at 4° C. against 1800 mL of buffer B over-night, followed by dialysis at 4° C. against 4×500 mL of potassium phosphate buffer (100 mM, pH 8.0) containing β-mercaptoethanol (0.25 mM) (buffer C) at 1.5 h interval. An aliquot (1 μL) of the dialyzed solution was assayed to confirm that there was no enzyme activity remaining. To the dialyzed solution of enzyme (apo-GABA-AT) was added a solution of PLP (40 μL, 20 mM) and [$^3$H]PLP (⅕ the amount prepared above) and stirred at rt for 5 h until the enzyme activity returned and the reactivation was complete. The excess [$^3$H]PLP was removed from the reconstituted GABA-AT solution by centrifugation with 5×400 μL of buffer C using a 10K molecular weight cutoff filter. The resulting enzyme solution was dialyzed at 4° C. against 2 L of buffer A overnight, affording the [$^3$H]PLP-reconstituted GABA-AT solution.

Example 27

Inactivation of [7-$^3$H]PLP-Reconstituted GABA-AT by 17 and Cofactor Analysis

A 60 μL portion of buffer A containing [7-$^3$H]PLP-reconstituted GABA-AT (⅕ the amount prepared above), α-ketoglutarate (3 mM), and 17 (4 mM) was protected from light and incubated at rt overnight until the activity of GABA-AT was less than 1%. To the inactivated enzyme solution was added KOH (1 drop, 1 M) to adjust the pH to 11. The mixture was allowed to stand at rt for 1 h, then trifluoroacetic acid (TFA) (6.7 μL) was added, and it was allowed to stand for another 5 min. The resulting denatured enzyme solution was centrifuged at 13,400 rpm for 5 min. The supernatant was collected, and the pellet was rinsed with 2×50 μL of buffer A containing 10% TFA and centrifuged. The supernatant and rinses were combined and lyophilized. The resulting solid was dissolved in 100 μL of a solution containing 1 mM PLP and 1 mM PMP standards and injected into an HPLC with an Econosil C18 column (4.6 mm×150 mm, 10μ). Water (with 0.1% TFA) and acetonitrile (with 0.1% TFA) were used as the mobile phase (0% acetonitrile, 0.5 mL/min, 25 min; then gradient to 90% acetonitrile, 1.0 mL/min, 30 min). Under these conditions, PMP eluted at 8 min and PLP at 13 min. Fractions were collected every minute, and the radioactivity was measured by liquid scintillation counting.

Example 28

Metabolomics of the Inactitaved GABA-AT

A 50 μL portion of ammonium bicarbonate buffer (50 mM, pH 7.4) containing GABA-AT (23 μg, 0.21 nmol), α-ketoglutarate (5 mM), and 17 (43 mM) was protected from light and incubated at rt overnight until the activity of GABA-AT was less than 1%. Another 50 μL of ammonium bicarbonate buffer (50 mM, pH 7.4) containing GABA-AT (23 μg, 0.21 nmol) and α-ketoglutarate (5 mM) was subjected to the same condition as a control. After incubation, formic acid (10 μL) was added to each sample, and 20 μL of each resulting solution was loaded onto a 5-μm Luna C18 column (2 mm i.d.; 150 mm) (Phenomenex, Torrance, Calif., USA). A 30-min LC gradient was employed at a flow rate of 200 μl/min on an Agilent 1150 LC system (Agilent, Santa Clara, Calif., USA). Mass spectrometry was performed on a Q-Exactive mass spectrometer (Thermo Fisher Scientific, Waltham, Mass., USA). Intact MS spectra were acquired at a resolution of 35,000. The top-five most intense ions were selected for fragmentation in a data-dependent acquisition mode. Mass spectra were acquired at a resolution of 17,500.

Example 29

Crystallization and Data Collection

Potassium pyrophosphate buffer (500 μL, 50 mM, pH 8.5) containing GABA-AT (200 μg, 1.82 nmol), α-ketoglutarate (5 mM), β-mercaptoethanol (5 mM), and 17 (37 mM) was protected from light and incubated at rt overnight until the activity of GABA-AT was less than 3%. The inactivated GABA-AT was then buffer-exchanged into a sodium acetate buffer (40 mM, pH 5.5) by centrifugation before the initial crystallization screening and optimization. The crystals were obtained in hanging drops comprising 1 μL of 10 mg/mL inactivated GABA-AT and 1 μL reservoir solution, containing 0.1 M ammonium acetate, 0.1 M Bis-Tris (pH 5.5), and 17% w/v PEG 10,000. Diffraction quality crystals grew within 4-5 days at ambient temperature. For X-ray data collection, these crystals were briefly soaked in the reservoir solution with additional 20% (v/v) glycerol as cryo-protectant before flash freezing in liquid nitrogen. Crystallographic data were collected on beamlines 23ID-B and 23ID-D of GM/CA@APS of the Advanced Photon Source (APS) using X-rays of 0.99 Å wavelength and Rayonix (formerly MAR-USA) 4×4 tiled CCD detector with a 300 mm² sensitive area. All data were indexed, integrated, and scaled with HKL2000.

Example 30

Phasing, Model Building, and Refinement

Molecular replacement for the inactivated GABA-AT was carried out using the program Phaser from CCP$_4$ software suite. The tetrameric structure of native GABA-AT from human brain was used as starting search model, in which all solvent and PLP molecules were deleted. Initial $R_{free}$ and R factor of the correct solution were 29.59% and 28.91%, respectively. The rigid body refinement was followed by restrained refinement with Refmac5 and further manual model inspection and adjustments with Coot. When refinement converged, the Fo-Fc difference maps, before incorporation of ligands in the structures, show a well-defined electron density for both PLP and the inactivator tetrahydrothiophene (FIG. 4A). The structure of inactivator tetrahydrothiophene was built in Chemdraw (a "Mol" file); the molecule was regularized and then the chemical restrains were generated in program JLigand. The PLP and the inactivator were fitted into the residual electron density in COOT after the rest of the structure, including most of the solvent molecules, had been refined. The $R_{free}$ and $R_{factor}$ for inactivated GABA-AT were 21.5% and 19.8%, respectively. All structural figures were made in UCSF Chimera.

Example 31

The molecular modeling studies of the PLP adducts with 39, 40, and 41 were performed using the GOLD software package, version 5.3 (Cambridge Crystallographic Data Center, Cambridge, UK). The X-ray coordinates of adduct 34 bound to GABA-AT were used, and the active site was defined as a sphere enclosing residues within 10 Å around 34. The 3D structures of 39, 40, and 41 were built using ChemBio Ultra (version 14.0) and were energy minimized using an MM2 force field for 1000 iterations and a convergence value of 0.01 kcal/mol/Å as the termination criterion. The energy minimized PLP-39, PLP-40, and PLP-41 complexes were docked in the binding site of GABA-AT (without 34) and scored using ChemPLP fitness function. All poses generated by the program were visualized; however, the pose with the highest fitness score was used for elucidating the binding characteristics of 39, 40, and 41 in the GABA-AT active site. Pymol (version 1.1) was used for generating the image in FIG. 7.

Example 32

Inhibition of the hERG Channel

The experiments were performed by Eurofins Panlabs (Redmond, Wash. 98052, USA). hERG CHO-K1 cell line was used. The test concentrations were 0.1 µM, 1 µM, and 10 µM. The incubation time was 5 min at room temperature, cumulatively. The detection method used an automated whole-cell patch clamp. The experiments were duplicated, and the % inhibition of the tail current was averaged (FIG. 9).

Example 33

Inhibition of Microsomal Cytochromes P450

The experiments were performed by Eurofins Panlabs (Redmond, Wash. 98052, USA). CYP1A inhibition (HLM, phenacetin substrate), CYP2B6 inhibition (HLM, bupropion substrate), CYP2C8 inhibition (HLM, paclitaxel substrate), CYP2C9 inhibition (HLM, diclofenac substrate), CYP2C19 inhibition (HLM, omeprazole substrate), CYP2D6 inhibition (HLM, dextromethorphan substrate), and CYP3A inhibition (HLM, midazolam and testosterone substrates) were tested. The test concentration was 10 µM. The incubation time was 10 min at 37° C. The detection method was by HPLC-MS/MS. The experiments were duplicated, and the % inhibition of the control values was averaged (FIG. 10).

Example 34

Metabolic Stability in Human Liver Microsomes

The experiments were performed by Eurofins Panlabs (Redmond, Wash. 98052, USA). The test concentration of 17 was 0.1 µM. The incubation time was 0, 15, 30, 45, and 60 min at 37° C. The detection method was by LC-MS/MS. Imipramine, propranolol, terfenadine, and verapamil were run in similar condition as controls.

As demonstrated, this invention is directed to a new class of GABA-AT inactivators. Preliminary in vitro results show that 17 is eight times more efficient an inactivator of GABA-AT than vigabatrin, an FDA-approved antiepilepsy drug, and 18 is half as efficient as vigabatrin. Mechanistic studies of the inactivation of GABA-AT by 17 showed that the sulfur atom in 17 plays a role in keeping the resulting adduct bound to the active site of GABA-AT, thereby inactivating the enzyme. An intermolecular nonbonded interaction between the carboxyl oxygen of Glu-270 and the sulfur atom in 17, the first observed example of this kind, is believed to be a factor in stabilizing adducts of this sort in the enzyme active site.

We claim:
1. A compound of a formula

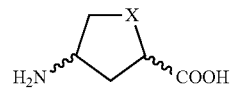

wherein X is selected from S and $SO_2$, or a salt thereof.
2. The compound of claim 1 wherein X is S.
3. The compound of claim 2 of a formula

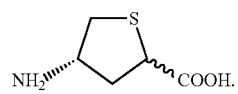

4. The compound of claim 3 wherein said amino and carboxy substituents have a cis stereochemical relationship.
5. The compound of claim 1 wherein said compound is an ammonium salt.
6. The compound of claim 5 wherein the counter ion of said salt is the conjugate base of a protic acid.
7. A compound of a formula

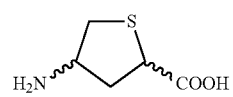

wherein said amino and carboxy substituents have a stereochemical relationship selected from cis and trans, or a salt thereof.

8. The compound of claim 7 of a formula

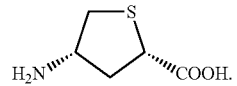

9. The compound of claim 8 wherein said compound is a salt comprising an ammonio substituent, a carboxylate substituent or a combination thereof.

10. The compound of claim 9 wherein said compound is an ammonium salt.

11. The compound of claim 10 wherein the counter ion of said salt is the conjugate base of a protic acid.

* * * * *